(12) United States Patent
Huang et al.

(10) Patent No.: US 12,331,417 B1
(45) Date of Patent: Jun. 17, 2025

(54) METHODS AND SYSTEMS FOR THE CONVERSION OF CARBON DIOXIDE TO CHEMICALS AND/OR FUELS UTILIZING STEAM ELECTROLYSIS

(71) Applicant: Chevron U.S.A. Inc., San Ramon, CA (US)

(72) Inventors: Zihan Huang, Emeryville, CA (US); Lin Li, San Ramon, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 50 days.

(21) Appl. No.: 18/538,342

(22) Filed: Dec. 13, 2023

(51) Int. Cl.
| | |
|---|---|
| *C25B 9/67* | (2021.01) |
| *B01J 19/00* | (2006.01) |
| *B01J 19/24* | (2006.01) |
| *C07C 29/152* | (2006.01) |
| *C07C 41/01* | (2006.01) |
| *C25B 1/042* | (2021.01) |
| *C25B 9/19* | (2021.01) |
| *C25B 15/08* | (2006.01) |

(52) U.S. Cl.
CPC ............. *C25B 9/67* (2021.01); *B01J 19/0013* (2013.01); *B01J 19/245* (2013.01); *C07C 29/152* (2013.01); *C07C 41/01* (2013.01); *C25B 1/042* (2021.01); *C25B 9/19* (2021.01); *C25B 15/081* (2021.01); *B01J 2219/00117* (2013.01); *B01J 2219/00157* (2013.01)

(58) Field of Classification Search
None
See application file for complete search history.

(56) References Cited

U.S. PATENT DOCUMENTS

| | | | |
|---|---|---|---|
| 9,631,284 B2 | 4/2017 | Braun et al. | |
| 10,421,913 B2 | 9/2019 | von Olshausen et al. | |
| 2014/0272734 A1 | 9/2014 | Braun et al. | |
| 2024/0204225 A1* | 6/2024 | Shinoki | H01M 8/04225 |
| 2025/0073695 A1* | 3/2025 | Li | C25B 1/23 |

FOREIGN PATENT DOCUMENTS

| | | |
|---|---|---|
| CN | 218934568 U | 4/2023 |
| WO | 2023172346 A1 | 9/2023 |
| WO | WO-2024027073 A1 * | 2/2024 |

OTHER PUBLICATIONS

Machine translation WO2024027073A1, Feb. 8, 2024, pp. 1-20 (Year: 2024).*

(Continued)

*Primary Examiner* — Medhanit W Bahta
(74) *Attorney, Agent, or Firm* — Michael E. Carmen; Terrence M. Flaherty

(57) ABSTRACT

A method includes heating a steam feed stream received from a reactor unit in a first heat exchanger using an anode effluent from an anode of an electrolyzer as a heat transfer medium to generate a first heated steam effluent, heating the first heated steam effluent in a second heat exchanger using a cathode effluent from a cathode of the electrolyzer as a heat transfer medium to generate a second heated steam effluent, combusting, in a combustion unit, a first tail gas stream to transfer heat to the second heated steam effluent to generate a third heated steam effluent, and passing the third heated steam effluent to the cathode of the electrolyzer.

18 Claims, 12 Drawing Sheets

(56) References Cited

OTHER PUBLICATIONS

PCT/US2024/048108, International Search Report, Jan. 21, 2025, 16 pages.
Becker, W. L., et al. "Production of Fischer-Tropsch liquid fuels from high temperature solid oxide co-electrolysis units." Energy 47.1 1, Oct. 23, 2012, pp. 99-115.
Herz, Gregor, Erik Reichelt, and Matthias Jahn. "Techno-economic analysis of a co-electrolysis-based synthesis process for the production of hydrocarbons." Applied Energy 21, 2, Feb. 20, 2018, pp. 309-320.
Herz, Gregor, et al. "Economic assessment of Power-to-Liquid processes-Influence of electrolysis technology and operating conditions." Applied Energy 292, 3, Apr. 8, 2021, 116655, pp. 1-18.

* cited by examiner

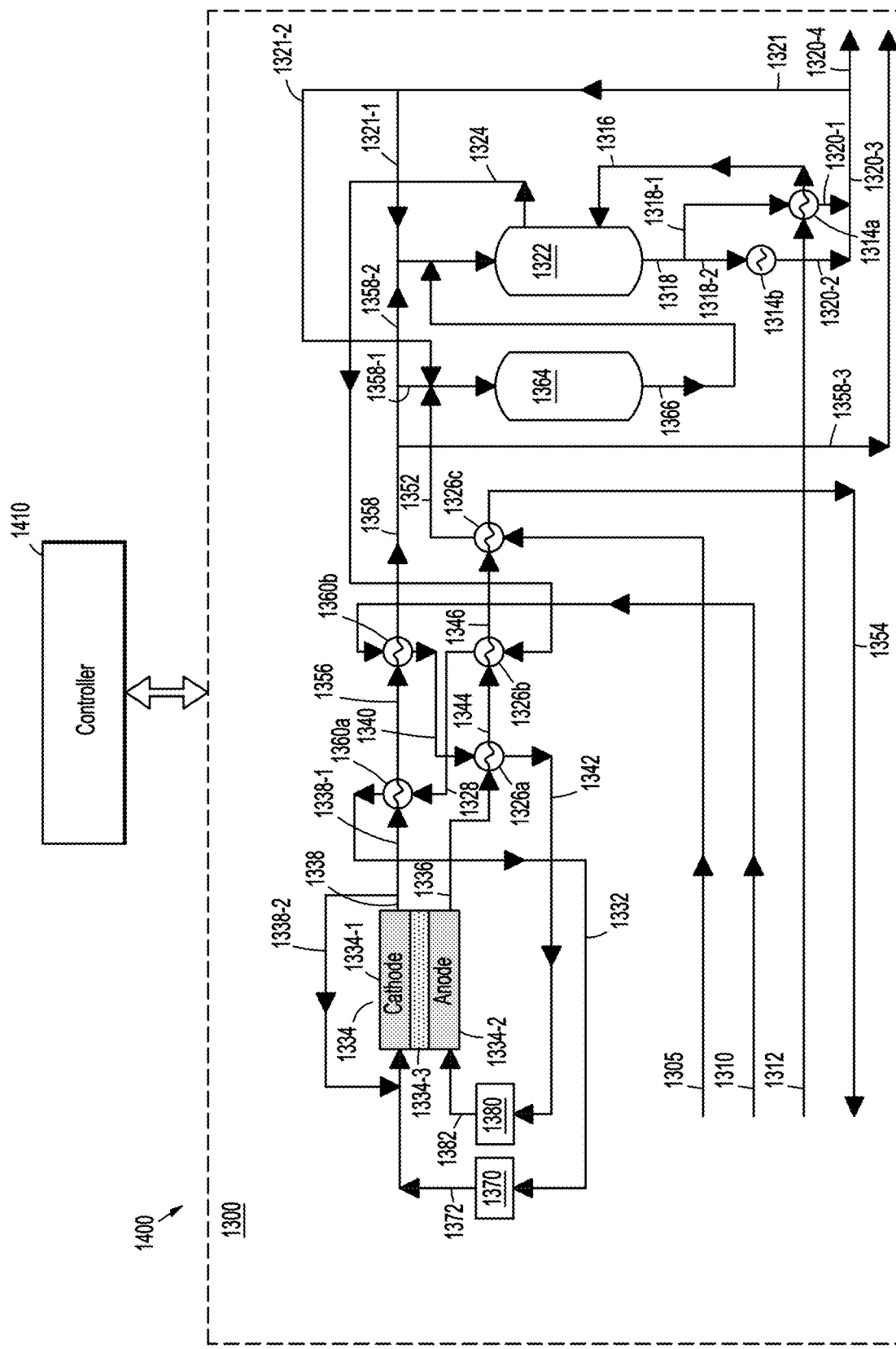

METHODS AND SYSTEMS FOR THE CONVERSION OF CARBON DIOXIDE TO CHEMICALS AND/OR FUELS UTILIZING STEAM ELECTROLYSIS

BACKGROUND

Many energy production processes release carbon dioxide. In order to reduce the climate-damaging effects of carbon dioxide in the atmosphere, the carbon dioxide can be converted into other substances. For example, carbon dioxide can be reduced to carbon monoxide by supplying energy. The carbon in carbon monoxide is in a lower oxidation state than in carbon dioxide, and, therefore, can be used for more applications than carbon dioxide. Accordingly, converting carbon dioxide into a chemical such as carbon monoxide not only reduces the amount of climate-damaging carbon dioxide, but also produces a valuable chemical raw material such as carbon monoxide.

Carbon dioxide can also be reduced to methanol. For example, carbon dioxide can be directly hydrogenated to methanol in the presence of a catalyst.

Producing a chemical using energy is also known as "Power-to-X" because energy ("power") can be used to obtain a chemical ("X"). By using climate-damaging carbon dioxide as a starting material, this concept can contribute to reducing global warming.

SUMMARY

In accordance with an illustrative embodiment, a method comprises:
heating a steam feed stream having a temperature of from about 250° C. to about 350° C. received from a reactor unit in a first heat exchanger using an anode effluent from an anode of an electrolyzer comprising an anode, a cathode, and an electrolyte inserted between the anode and the cathode as a heat transfer medium to generate a first heated steam effluent having a temperature of about 350° C. to about 450° C. and a cooled anode effluent,
heating the first heated steam effluent in a second heat exchanger using a cathode effluent from the cathode of the electrolyzer as a heat transfer medium to generate a second heated steam effluent having a temperature of about 550° C. to about 650° C. and a cooled cathode effluent,
combusting, in a combustion unit, a first tail gas stream to transfer heat to the second heated steam effluent to generate a third heated steam effluent having a temperature of about 700° C. to about 950° C., and passing the third heated steam effluent to the cathode of the electrolyzer.

In accordance with another illustrative embodiment, a method comprises:
heating a water feed stream in a first heat exchanger using a reactor synthesis
effluent including tail gas from a reactor unit as a heat transfer medium to generate a heated water effluent having a temperature of about 50° C. to about 150° C.,
performing an exothermic reaction in the reactor unit thereby transferring heat from the exothermic reaction to the heated water effluent to generate a steam feed stream having a temperature of about 250° C. to about 350° C.,
heating the steam feed stream in a second heat exchanger using an anode effluent from an anode of an electrolyzer comprising an anode, a cathode, and an electrolyte inserted between the anode and the cathode as a heat transfer medium to generate a first heated steam effluent having a temperature of about 350° C. to about 450° C. and a cooled anode effluent,
heating the first heated steam effluent in a third heat exchanger using a cathode effluent from the cathode of the electrolyzer as a heat transfer medium to generate a second heated steam effluent having a temperature of about 550° C. to about 650° C. and a cooled cathode effluent,
combusting, in a combustion unit, a first tail gas stream to transfer heat to the second heated steam effluent to generate a third heated steam effluent having a temperature of about 700° C. to about 950° C., and passing the third heated steam effluent to the cathode of the electrolyzer.

In accordance with yet another illustrative embodiment, a system comprises:
a first heat exchanger configured to heat a steam feed stream having a temperature of from about 250° C. to about 350° C. using an anode effluent from an anode of an electrolyzer comprising an anode, a cathode, and an electrolyte inserted between the anode and the cathode as a heat transfer medium to generate a first heated steam effluent having a temperature of about 350° C. to about 450° C. and a cooled anode effluent,
a second heat exchanger configured to heat the first heated steam effluent using a cathode effluent from a cathode of the electrolyzer as a heat transfer medium to generate a second heated steam effluent having a temperature of about 550° C. to about 650° C. and a first cooled cathode effluent, and
a combustion unit configured to combust a tail gas stream to transfer heat to the second heated steam effluent to generate a third heated steam effluent having a temperature of about 700° C. to about 950° C. for sending to the cathode of the electrolyzer to generate another cathode effluent and another anode effluent from the third heated steam effluent.

BRIEF DESCRIPTION OF THE DRAWINGS

In combination with the accompanying drawing and with reference to the following detailed description, the features, advantages, and other aspects of the implementations of the present disclosure will become more apparent, and several implementations of the present disclosure are illustrated herein by way of example but not limitation. In the accompanying drawings.

reaction unit and a steam electrolyzer, according to an alternative illustrative embodiment.

Figure 5:
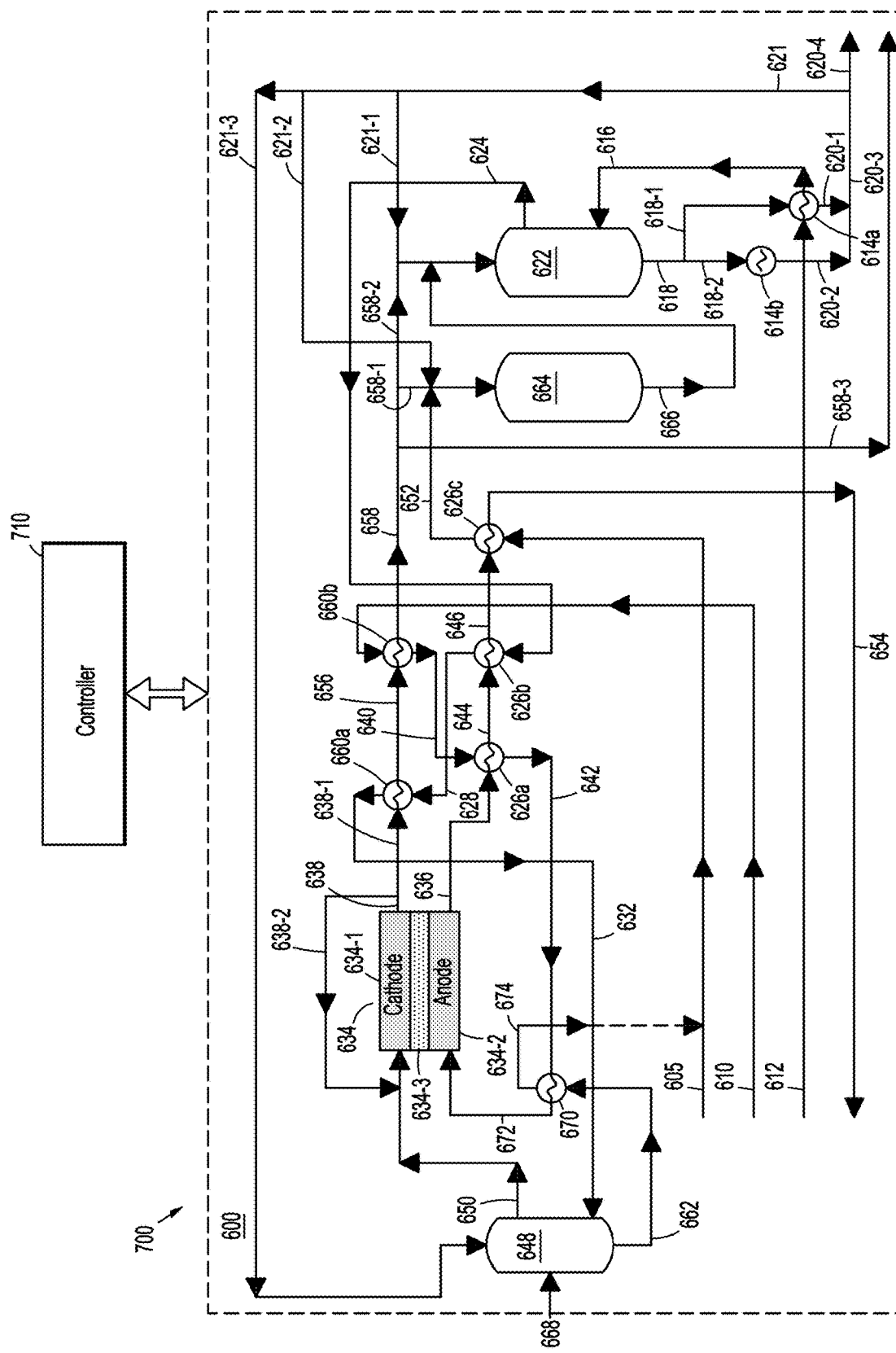

FIG. 5 illustrates a process flow diagram scheme with heat integration design including a combustion unit for a carbon dioxide conversion system for production of a Fischer-Tropsch product utilizing a reverse water gas shift (RWGS) reaction unit and a steam electrolyzer, according to an alternative illustrative embodiment.

Figure 6:
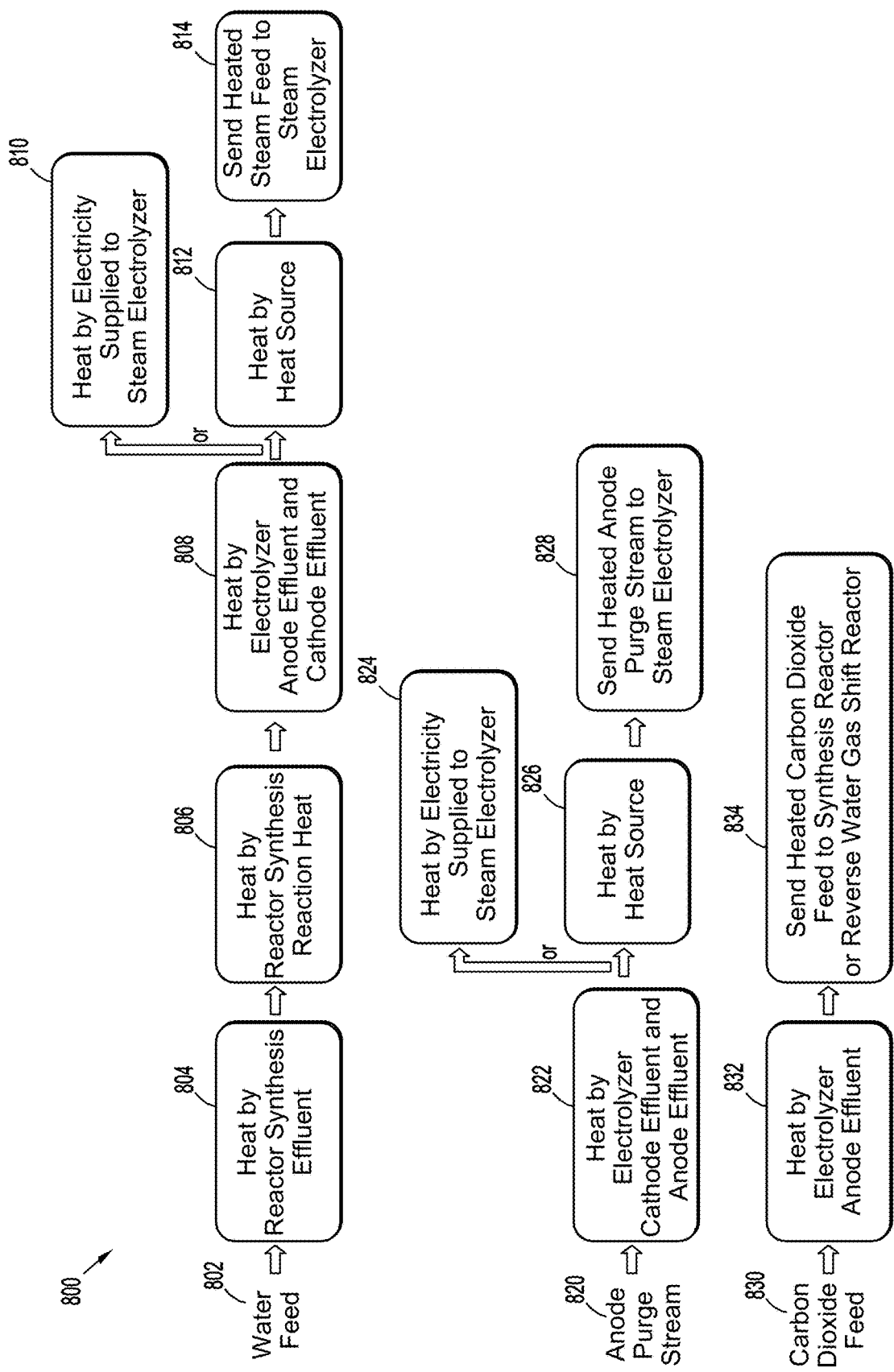

FIG. 6 is a flow chart illustrating a method utilizing the starting feed stream with heat integration design without a combustion unit for a carbon dioxide conversion system for production of methanol and dimethyl ether or a Fischer-Tropsch product, according to an alternative illustrative embodiment.

Figure 7A:
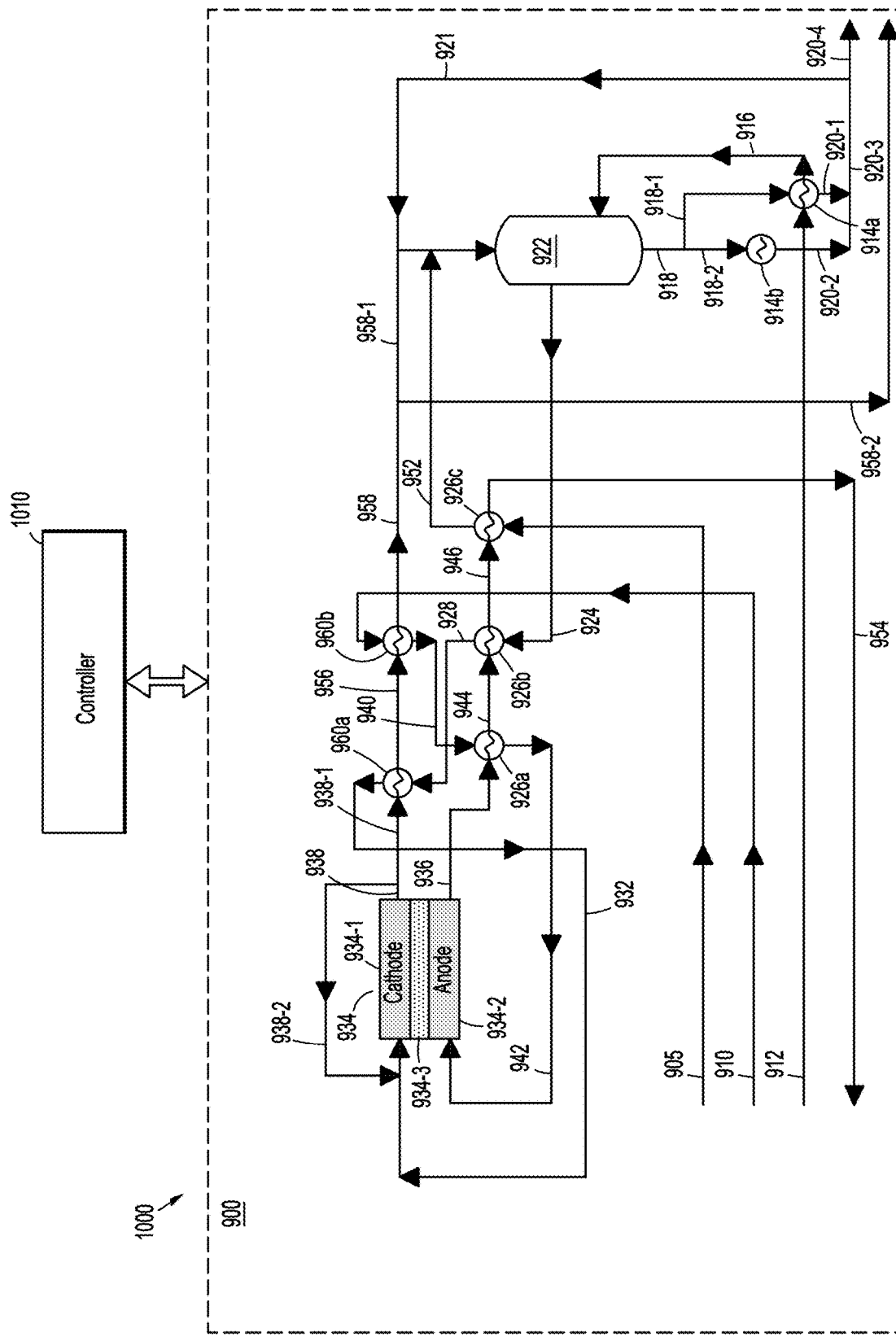

FIG. 7A illustrates a process flow diagram scheme with heat integration design without a combustion unit for a carbon dioxide conversion system for production of methanol/dimethyl ether, according to an illustrative embodiment.

Figure 7B:
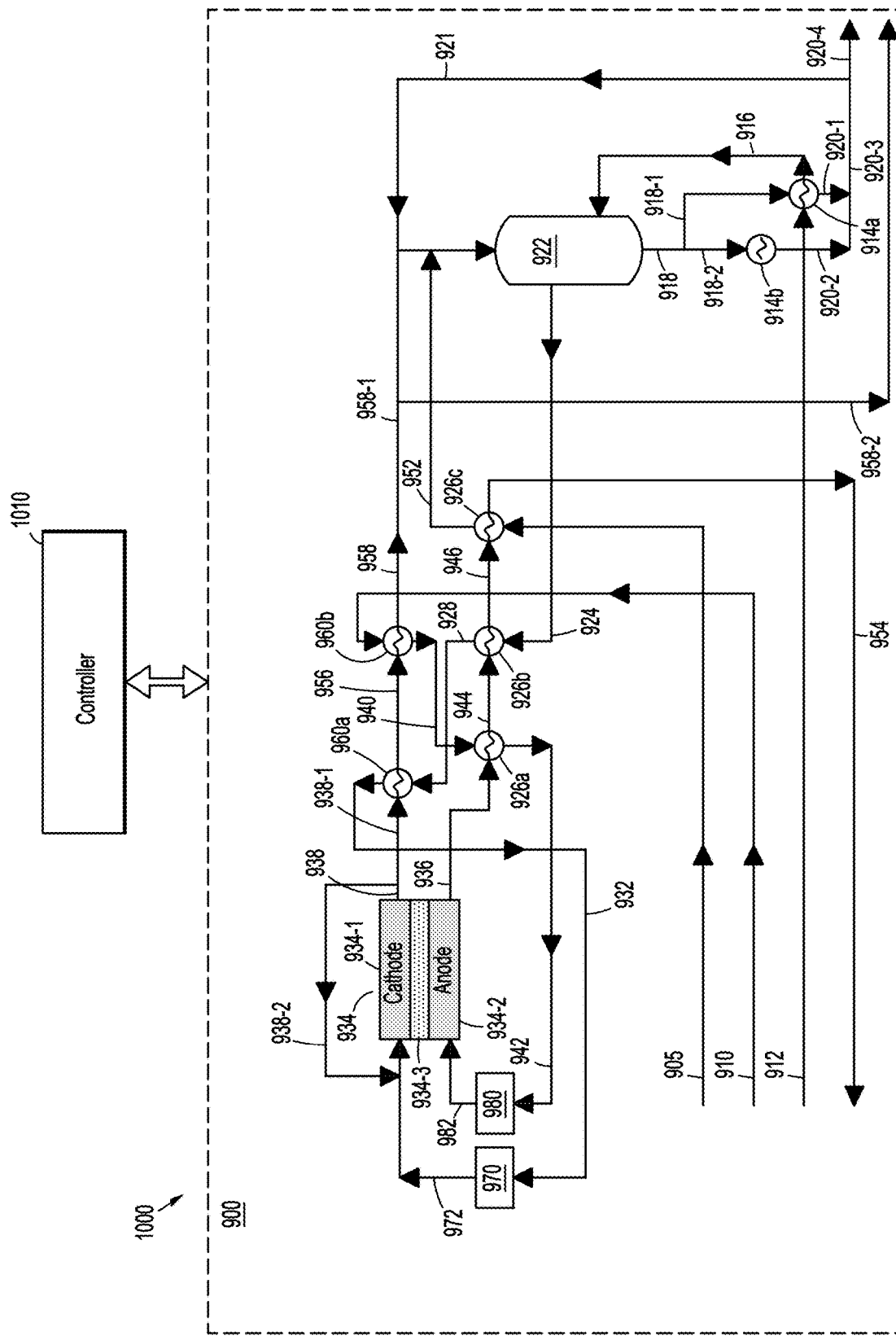

FIG. 7B illustrates a process flow diagram scheme with heat integration design without a combustion unit for a carbon dioxide conversion system for production of methanol/dimethyl ether, according to an alternative illustrative embodiment.

Figure 8A:
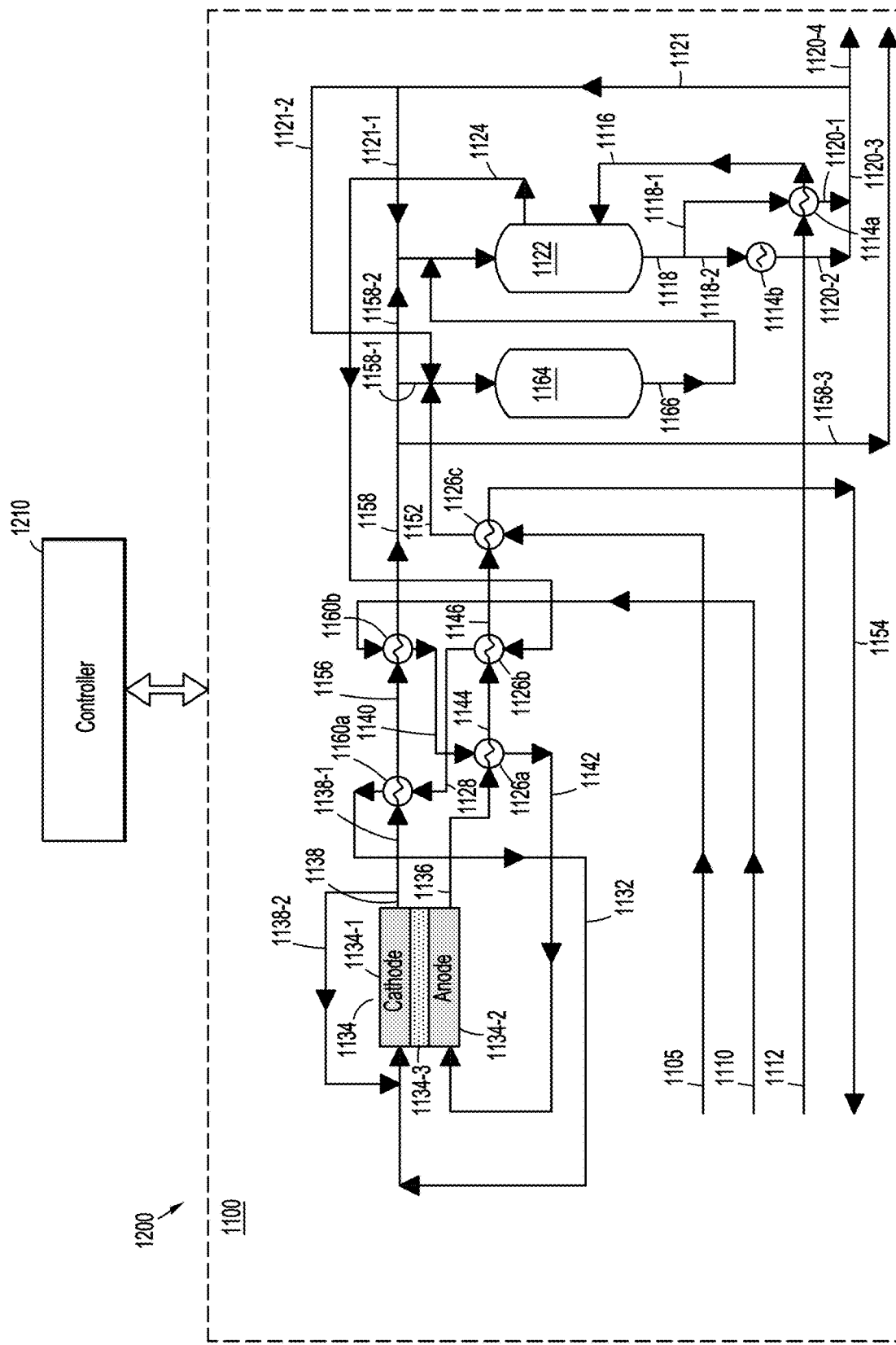

FIG. 8A illustrates a process flow diagram scheme with heat integration design without a combustion unit for a carbon dioxide conversion system for production of methanol/dimethyl ether utilizing a reverse water gas shift (RWGS) reaction unit and a steam electrolyzer, according to an illustrative embodiment.

Figure 8B:
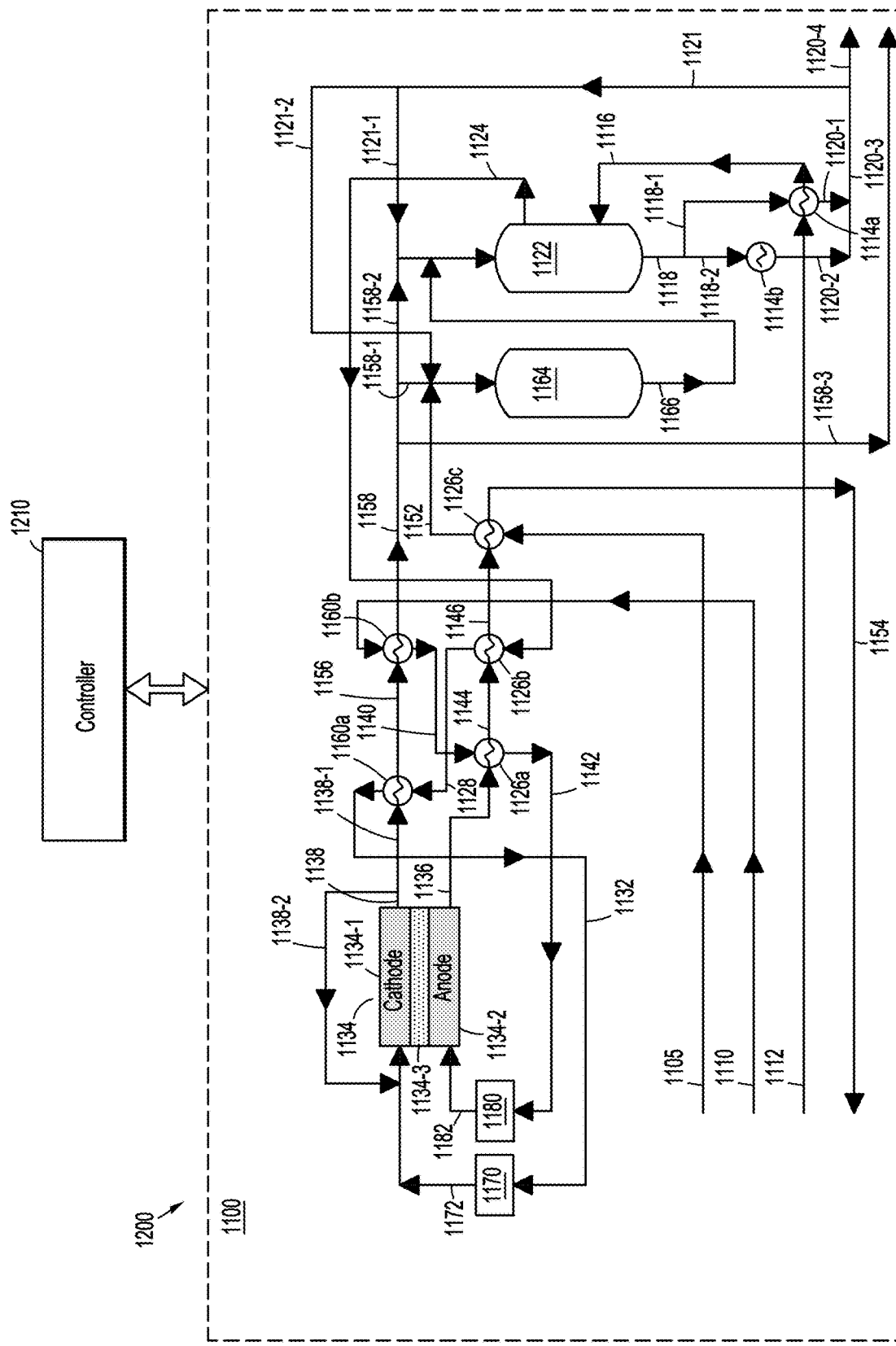

FIG. 8B illustrates a process flow diagram scheme with heat integration design without a combustion unit for a carbon dioxide conversion system for production of methanol/dimethyl ether utilizing a reverse water gas shift (RWGS) reaction unit and a steam electrolyzer, according to an alternative illustrative embodiment.

Figure 9A:
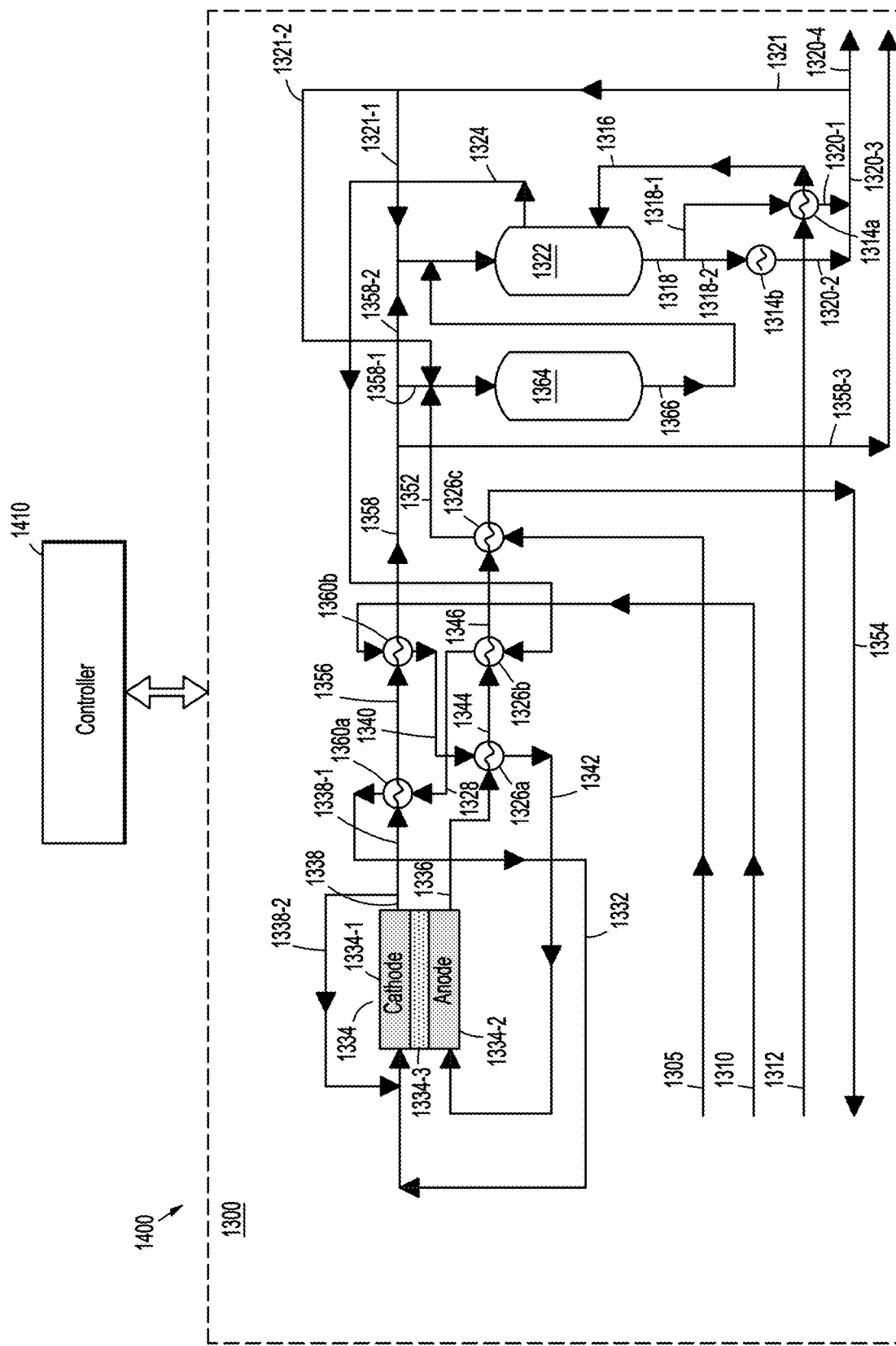

FIG. 9A illustrates a process flow diagram scheme with heat integration design without a combustion unit for a carbon dioxide conversion system for production of a Fischer-Tropsch product utilizing a reverse water gas shift (RWGS) reaction unit and a steam electrolyzer, according to an illustrative embodiment.

FIG. 9B illustrates a process flow diagram scheme with heat integration design without a combustion unit for a carbon dioxide conversion system for production of a Fischer-Tropsch product utilizing a reverse water gas shift (RWGS) reaction unit and a steam electrolyzer, according to an alternative illustrative embodiment.

DETAILED DESCRIPTION

Various illustrative embodiments described herein are directed to methods and systems for a carbon dioxide conversion system with heat integration to make chemicals and/or fuels. "Power-to-gas", "power-to-liquid", and "power-to-fuel" (referred to as "Power-to-X" processes) represent promising approaches for bringing about a future conversion from fossil energy sources to an energy infrastructure which is based mainly on renewable energy sources (RES), for example wind power, solar power, geothermal energy or water power. Electricity-based or synthetic fuels are becoming ever more important, particularly in the transport sector or in industry. Such fuels, for example methane, methanol or derivatives or downstream products such as kerosene, gasoline, diesel, or other hydrocarbon-based products are produced, in particular, by synthesis from hydrogen and carbon dioxide.

Power-to-X processes utilize electrical energy to convert carbon dioxide into carbon-neutral fuels or chemicals. For example, it is possible to convert carbon dioxide and water directly in an electrolyzer into multi-carbon species as desired fuels or chemicals. However, such a direct route is still at the early stage of development and faces significant technical challenges. On the other hand, the indirect route involves steam electrolysis, which is a more mature technology, to provide hydrogen which can react with either carbon dioxide or carbon monoxide (i.e., reduced from carbon dioxide via RWGS reaction) for fuel synthesis. However, the electrolysis of steam requires a large amount of energy. Accordingly, improving the energy efficiency of the Power-to-X process is critical to make the technology more economically feasible.

With energy available from renewable sources, the energy requirement of power-to-fuel process may still be high for large scale application, therefore it is critical for the system to achieve high energy efficiency for practical application. A critical area to help achieve high energy efficiency of the process is to provide enough thermal energy of material streams to a steam electrolyzer, e.g., heat each cold feed inlet of water, carbon dioxide and air, for operation of the steam electrolyzer using the available heat sources within the process and system via efficient heat integration design by reducing the consumption of external energy input.

The non-limiting illustrative embodiments disclosed herein of FIGS. 1-9B utilize heat integration design and the specific heat integration design of recovering heat from various heat sources of the method and system disclosed herein to heat the material streams to the steam electrolyzer to supply all thermal energy required to minimize the external electrical energy input (or maximize the overall process efficiency).

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology can be applied, as long as that definition does not conflict with any other disclosure or definition applied herein or render indefinite or non-enabled any claim to which that definition is applied. To the extent that any definition or usage provided by any document incorporated herein by reference conflicts with the definition or usage provided herein, the definition or usage provided herein controls.

While systems and methods are described in terms of "comprising" various components or steps, the systems and methods can also "consist essentially of" or "consist of" the various components or steps, unless stated otherwise.

The terms "a," "an," and "the" are intended to include plural alternatives, e.g., at least one. The terms "including", "with", and "having", as used herein, are defined as comprising (i.e., open language), unless specified otherwise.

Various numerical ranges are disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. For example, all numerical end points of ranges disclosed herein are approximate, unless excluded by proviso.

Values or ranges may be expressed herein as "about", from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In another aspect, use of the term "about" means±20% of the stated value, ±15% of the stated value, ±10% of the stated value, ±5% of the stated value, ±3% of the stated value, or ±1% of the stated value.

Applicant reserves the right to proviso out or exclude any individual members of any such group of values or ranges, including any sub-ranges or combinations of sub-ranges within the group, that can be claimed according to a range or in any similar manner, if for any reason Applicant chooses to claim less than the full measure of the disclosure, for example, to account for a reference that Applicant may be unaware of at the time of the filing of the application. Further, Applicant reserves the right to proviso out or exclude any members of a claimed group.

The term "electrode" is meant, in the sense of the present disclosure, an electronic conductor capable of capturing or releasing electrons. An oxidation reaction occurs at the anode, whereas a reduction reaction occurs at the cathode.

The term "electrolysis" is a technique that uses direct electric current to drive an otherwise non-spontaneous chemical reaction. For example, the electrolysis of water is the process of using electricity to electrochemically decompose water into oxygen and hydrogen. The term "electrolyzer," also called an "electrolysis device," refers to a unit where this chemical reaction may take place.

Although any processes and materials similar or equivalent to those described herein can be used in the practice or testing of the illustrative embodiments described herein, the typical processes and materials are herein described.

The non-limiting illustrative embodiments described herein overcome the drawbacks discussed above by providing methods and systems for carbon dioxide conversion to chemicals and/or fuels with electrochemical conversion of steam and applied heat integration. For example, the non-limiting illustrative embodiments described herein include a system-level process design with optimized heat integration of a steam electrolyzer coupled with a downstream synthesis reaction process, from which the overall system efficiency is enhanced by leveraging the available heat sources in the system. Accordingly, the non-limiting illustrative embodiments described herein are able to maximize the utilization of the available heat sources to generate steam and heat the feed streams being sent to the steam electrolyzer, thereby reducing the electrolyzer electricity consumption while improving energy efficiency and reducing electricity cost.

The illustrative embodiments of the present disclosure will be specifically described below with reference to the accompanying drawings. For the purpose of clarity, some steps leading up to the carbon dioxide and steam conversion to chemicals and/or fuels as illustrated in FIGS. 1-9B are omitted such as compression of feed streams to fuel synthesis reactors. In other words, one or more well-known processing steps which are not illustrated but are well-known to those of ordinary skill in the art have not been included in the figures. This is not intended to be interpreted as a limitation of any particular embodiment, or illustration, or scope of the claims.

Figure 1:
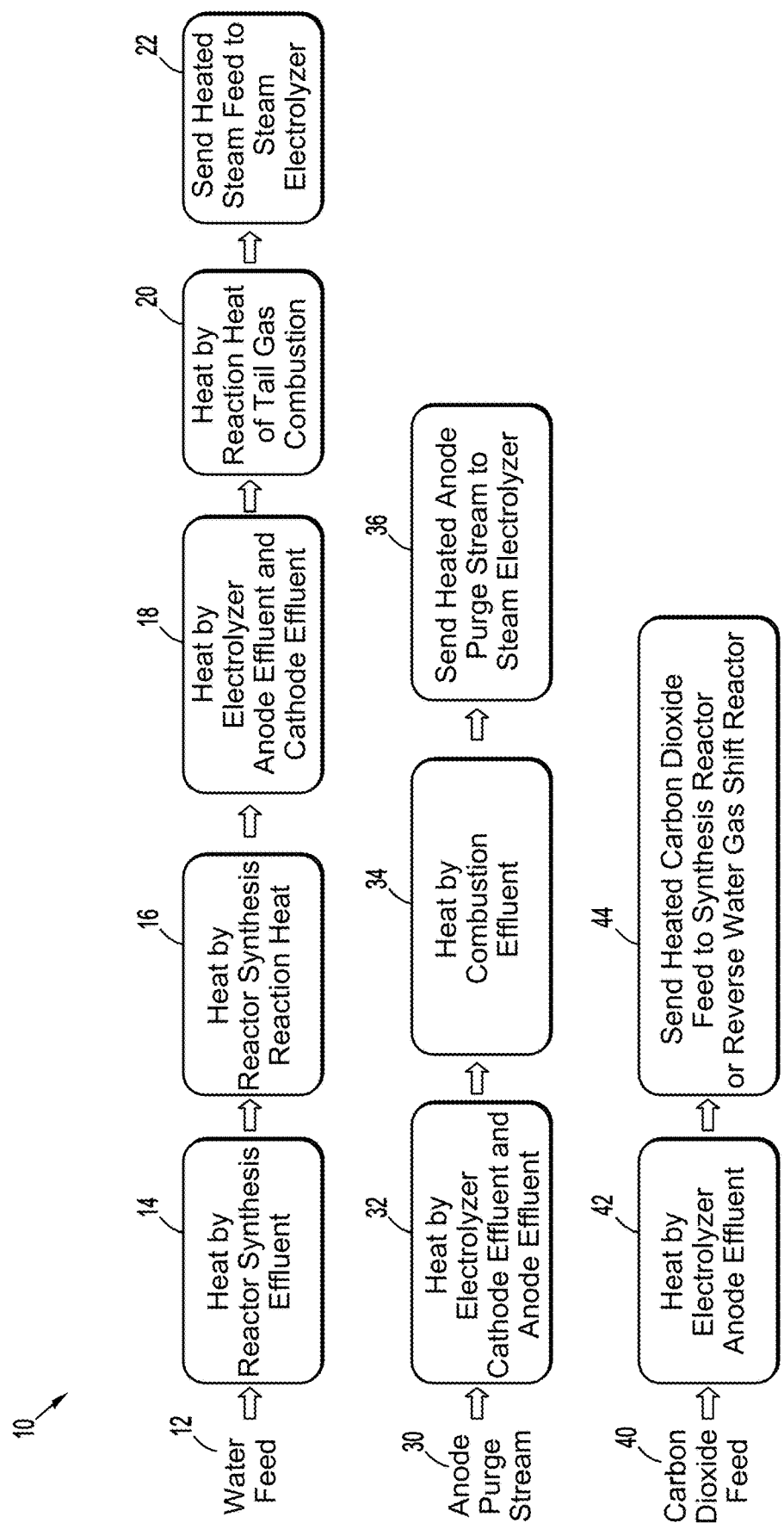
FIG. 1 is a flow chart illustrating a method utilizing the starting feed streams with heat integration design including a combustion unit for a carbon dioxide conversion system for production of methanol and dimethyl ether or a Fischer-Tropsch product, according to an illustrative embodiment.

FIG. 1 illustrates a flow chart of method 10 for each of the starting feed streams including water feed 12, anode purge stream 30 and carbon dioxide feed 40. In a non-limiting illustrative embodiment, the method utilizing the starting feed streams can be carried out in parallel. Method 10 for the conversion of carbon dioxide and steam for the production of chemical products such as methanol and dimethyl ether and/or fuels according to the illustrative embodiments of the present disclosure will now be described with reference to FIGS. 2-5 in combination with FIG. 1. FIGS. 2-5 illustrate heat integration design including a combustion unit for a carbon dioxide conversion system. For ease of understanding, specific examples mentioned in the following description are all illustrative and are not used to limit the scope of the present disclosure.

In an illustrative embodiment, one of the starting streams is water feed 12 at or around a temperature of about 20° C.

Step 14 of method 10 includes water feed 12 being heated by reactor synthesis effluent to generate a heated water stream having a temperature of 50° C. to about 150° C.

Step 16 of method 10 includes heated water stream being heated by reactor synthesis reaction heat to generate a steam feed stream having a temperature of from about 250° C. to about 350° C.

Step 18 of method 10 includes steam feed stream being heated by an electrolyzer anode effluent and an electrolyzer cathode effluent to generate a first heated steam feed stream having a temperature of from about 550° C. to about 650° C.

Step 20 of method 10 includes first heated steam feed stream being heated by combustion of tail gas to generate a second heated steam feed stream having a temperature of from about 750° C. to about 850° C.

Step 22 of method 10 includes sending the second heated steam feed stream to a steam electrolyzer.

In an illustrative embodiment, one of the starting streams is anode purge stream 30 at or around a temperature of about 20° C. As discussed below, representative examples of anode purge stream 30 include one or more of air, carbon dioxide or an inert gas such as $N_2$.

Step 32 of method 10 includes anode purge stream 30 being heated by an electrolyzer cathode effluent and an electrolyzer anode effluent to generate a first heated anode purge stream.

Step 34 of method 10 includes heating first heated anode purge stream with the combustion effluent to generate a second heated anode purge stream.

Step 36 of method 10 includes sending the second heated anode purge stream to the anode of the steam electrolyzer.

In an illustrative embodiment, one of the starting streams is carbon dioxide feed 40 at or around a temperature of about 20° C.

Step 42 of method 10 includes carbon dioxide feed 40 being heated by an electrolyzer anode effluent to generate a heated carbon dioxide feed stream.

Step 44 of method 10 includes sending the heated carbon dioxide feed stream to a synthesis reactor or reverse water gas shift reactor.

Figure 2:
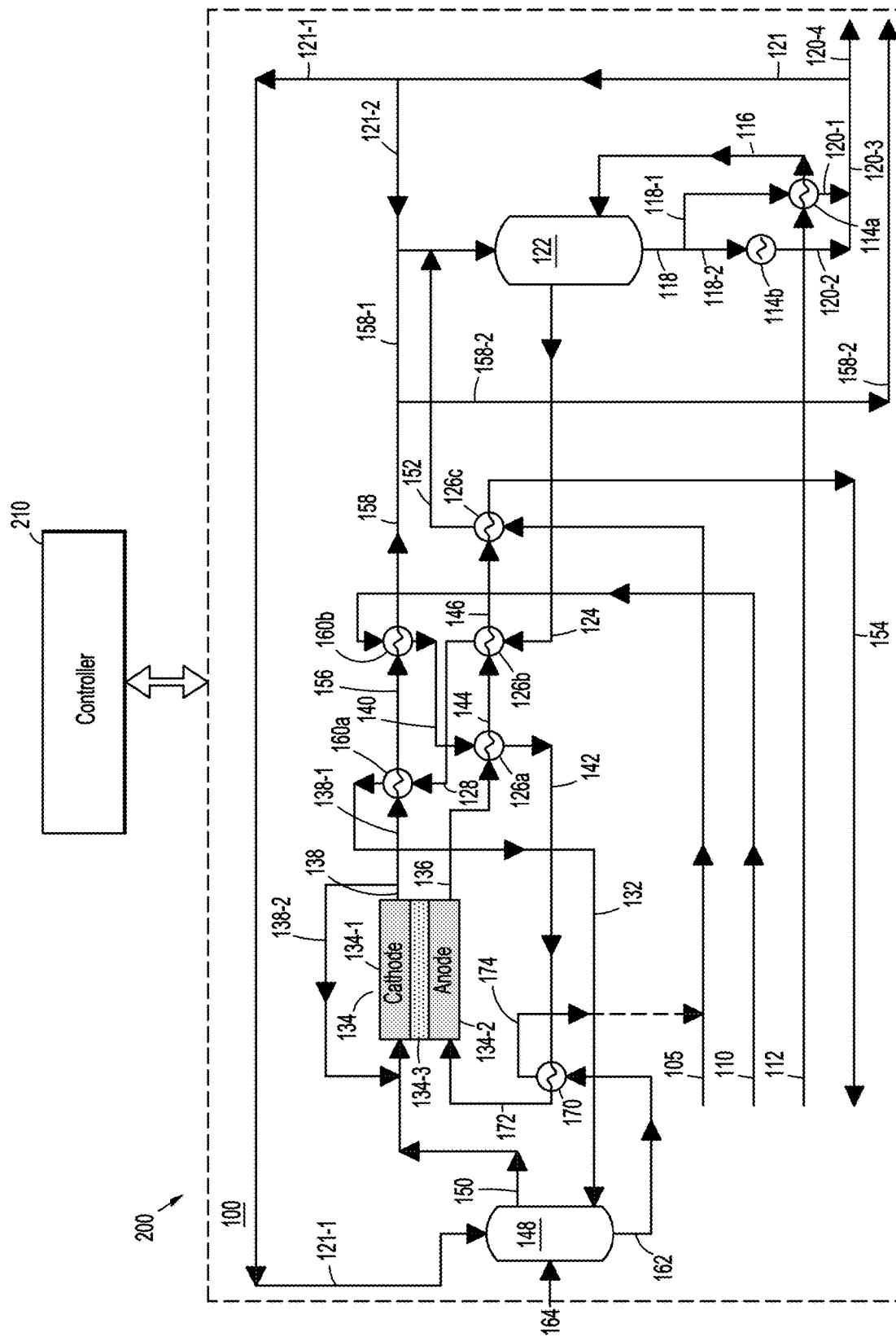
FIG. 2 illustrates a process flow diagram scheme with heat integration design including a combustion unit for a carbon dioxide conversion system for production of methanol/dimethyl ether, according to an alternative illustrative embodiment.

FIG. 2 illustrates a method and system diagram with heat integration design for the conversion of carbon dioxide to produce chemicals such as methanol and dimethyl ether and/or fuels. Referring now to FIG. 2, system 100 includes heat exchanger 114a for receiving water feed stream 112 at or around room temperature, i.e., about 20° C., and a first portion 118-1 of reactor synthesis effluent 118 from reactor unit 122 as a heat transfer medium to generate a heated water feed stream effluent 116 having a temperature of about 50° C. to about 150° C. and a cooled reactor synthesis effluent 120-1. As will be discussed below, reactor synthesis effluent 118 exiting from reactor unit 122 can be any product produced from heated carbon dioxide effluent 152, hydrogen from first portion 158-1 of second cooled cathode effluent 158 and second reactor tail gas 121-2 composed primarily of gaseous by-products, such as methane and carbon monoxide and water, and unconverted feed carbon dioxide and hydrogen. The products produced in reactor unit 122 can be, for example, methanol and dimethyl ether, or hydrocarbons from direct hydrogenation of carbon dioxide and hydrogen, undesired by-products such as methane and water, and unconverted feeds ($CO_2$ and $H_2$). However, this is merely illustrative and any other chemical product that can be made from direct hydrogenation of heated carbon dioxide effluent 152, hydrogen from first portion 158-1 of second cooled cathode effluent 158 and second reactor tail gas 121-2 is contemplated herein for use as reactor synthesis effluent 118.

In some embodiments, heat exchanger 114a may be a shell-and-tube, plate-fin, microchannel, spiral wound, or any other suitable heat exchanger. The reactor synthesis effluent 118 from reactor unit 122 is a heated reactor synthesis effluent 118 having a temperature of from about 250° C. to about 350° C. which is split into first portion 118-1 and second portion 118-2. Accordingly, first portion 118-1 of reactor synthesis effluent 118 delivers the heat in heat exchanger 114a to water feed stream 112 to generate a heated water feed stream effluent 116, and the first portion 118-1 of reactor synthesis effluent 118 is likewise cooled against water feed stream 112 in heat exchanger 114a which cools first portion 118-1 of reactor synthesis effluent 118 to generate a cooled reactor synthesis effluent 120-1, i.e., a temperature of less than 250° C. such as from about 150° C. to about 230° C.

System 100 further includes heat exchanger 114b for receiving second portion 118-2 of reactor synthesis effluent 118 from reactor unit 122 and cooling second portion 118-2 of reactor synthesis effluent 118 to generate a cooled reactor synthesis effluent 120-2 having a temperature of from about 150° C. to about 250° C. In some embodiments, heat exchanger 114b may be a shell-and-tube, plate-fin, microchannel, spiral wound, or any other suitable heat exchanger. In this particular embodiment, cooled reactor synthesis effluent 120-1 and cooled reactor synthesis effluent 120-2 are combined into product stream 120-3 which contains desired products as discussed above, such as methanol and dimethyl ether, or hydrocarbons from direct hydrogenation of carbon dioxide and hydrogen, undesired by-products such as methane and water, and unconverted feeds ($CO_2$ and $H_2$). The product stream 120-3 is separated into product stream 120-4 containing the desired products as a liquid and reactor tail gas 121 which contains gaseous by-product and unconverted feeds as discussed below. The product stream 120-4 can be sent for further downstream processing as known in the art. For example, product stream 120-4 can be sent for further downstream processing for creating high value liquid fuels, such as gasoline, diesel, and jet. In some embodiments, heat exchanger 114b can also be used to heat the second reactor tail gas 121-2 before being recycled to the reactor unit 122.

Reactor tail gas 121 separated from product stream 120-3 has a temperature of from about 30° C. to about 80° C. and is split into first reactor tail gas 121-1 and second reactor tail gas 121-2 each composed primarily of gaseous by-products, such as methane and carbon monoxide, and unconverted carbon dioxide and hydrogen feeds. First reactor tail gas 121-1 is sent to the combustion unit 148 and combusted to provide thermal energy (i.e., heat) to transfer heat to the second heated steam effluent 132 received from heat exchanger 160a to generate a third heated steam effluent 150 for sending to the cathode 134-1 of electrolyzer 134 as a continuous loop in the process and system of the illustrative embodiments as discussed below. In addition, second reactor tail gas 121-2 can be recycled back to reactor unit 122 for further processing to enhance overall $CO_2$ utilization efficiency.

System 100 further includes reactor unit 122 for receiving heated water feed stream effluent 116, second reactor tail gas 121-2, heated carbon dioxide effluent 152 and first portion 158-1 of second cooled cathode effluent 158 composed of at least hydrogen with residual steam as discussed below. In non-limiting illustrative embodiments, reactor unit 122 is a synthesis reactor for converting carbon dioxide and hydrogen to desired products such as methanol which can thereafter be converted to, for example, dimethyl ether, in the same or separate reactor (not shown) by conventional techniques, e.g., by methanol synthesis and in-situ dehydration, in which the in-situ methanol conversion can alleviate the thermodynamic limits of methanol synthesis, resulting in higher dimethyl ether yield. The produced methanol/dimethyl ether products can be purified and collected following conventional fractional distillation, while a portion of any unreacted syngas (also referred to as tail gas) can be recycled (see second reactor tail gas 121-2) back to reactor unit 122 as discussed above.

The heated carbon dioxide effluent 152 will enter reactor unit 122 having a temperature from about 250° C. to about 350° C. and first portion 158-1 of second cooled cathode effluent 158 will enter reactor unit 122 having a temperature from about 250° C. to about 350° C. Accordingly, the reaction in reactor unit 122 utilizing at least second reactor tail gas 121-2, heated carbon dioxide effluent 152 and first portion 158-1 of second cooled cathode effluent 158 for making desired products such as, for example, methanol, is an exothermic reaction creating reaction heat to further heat and vaporize the incoming heated water feed stream effluent 116 thereby generating steam feed stream 124 having a temperature of from about 250° C. to about 350° C. The products produced from the reaction process can then be discharged from reactor unit 122 as reactor synthesis effluent 118. Accordingly, for purposes of this illustrative embodiment, reactor synthesis effluent 118 is one or more of methanol and/or dimethyl ether as well as unconverted feeds and by-products such as methane as discussed above. However, this is merely illustrative and any other product that can be made from the conversion of carbon dioxide and hydrogen is contemplated herein for use as reactor synthesis effluent 118.

System 100 further includes heat exchangers 126a, 126b and 126c. Heat exchanger 126a receives first heated anode purge stream 140 and anode effluent 136 from the anode 134-2 of electrolyzer 134 as a heat transfer medium to generate a second heated anode purge stream 142 for sending to the anode 134-2 of electrolyzer 134 and a first cooled anode effluent 144 for sending to heat exchanger 126b as discussed below. The anode effluent 136 exits the anode 134-2 of electrolyzer 134 having a temperature of from about 750° C. to about 850° C. and acts as a heat transfer medium in heat exchangers 126a and 126b. Accordingly, anode effluent 136 delivers the heat in heat exchanger 126a to first heated anode purge stream 140 and generates second heated anode purge stream 142 having a temperature of from about 550° C. to about 650° C. The second heated anode purge stream 142 can be further heated to about 750° C. to about 850° C. (as third heated anode purge stream 172) utilizing combusted stream 162 from the combustion unit 148 as discussed below to be sent to the anode 134-2 of electrolyzer 134 as depicted in FIG. 2, and the anode effluent 136 is likewise cooled against first heated anode purge stream 140 in heat exchanger 126a to generate a first cooled anode effluent 144 having a temperature of from about 580° C. to about 680° C. In some embodiments, heat exchanger 126a may be a shell-and-tube, plate-fin, microchannel, spiral wound, or any other suitable heat exchanger.

Heat exchanger 126b receives steam feed stream 124 and first cooled anode effluent 144 as a heat transfer medium to generate a first heated steam effluent 128 for sending to heat exchanger 160a and a second cooled anode effluent 146 for sending to heat exchanger 126c as discussed below. In other word, first cooled anode effluent 144 delivers the heat in heat exchanger 126b to steam feed stream 124 and generates first heated steam effluent 128 having a temperature of from about 350° C. to about 450° C., and the first cooled anode effluent 144 is likewise cooled against steam feed stream 124 in heat exchanger 126b to generate a second cooled anode effluent 146 having a temperature of from about 350° C. to about 450° C. In an illustrative embodiment, when anode purge stream 110 is air, then second cooled anode effluent 146 will be composed primarily of oxygen enriched air, e.g., about 50% $O_2$. As another example, when anode purge stream 110 is carbon dioxide, then second cooled anode effluent 146 will be composed of carbon dioxide and oxygen. In some embodiments, heat exchanger 126b may be a shell-and-tube, plate-fin, microchannel, spiral wound, or any other suitable heat exchanger.

Heat exchanger 126c receives carbon dioxide stream 105 having a temperature at or around 20° C. and second cooled anode effluent 146 as a heat transfer medium to generate a heated carbon dioxide effluent 152 for sending to reactor unit 122 as discussed above and a third cooled anode effluent 154 which exits the system as an air stream either vented or used as an oxygen enriched stream for combustion processes. In other word, second cooled anode effluent 146 delivers the heat in heat exchanger 126c to carbon dioxide stream 105 and generates heated carbon dioxide effluent 152 having a temperature of from about 250° C. to about 350° C., and the second cooled anode effluent 146 is likewise cooled against carbon dioxide stream 105 in heat exchanger 126c to generate a third cooled anode effluent 154 having a temperature of from about 250° C. to about 350° C. In some embodiments, heat exchanger 126c may be a shell-and-tube, plate-fin, microchannel, spiral wound, or any other suitable heat exchanger.

A carbon dioxide source in the present disclosure for carbon dioxide stream 105 can be obtained from several sources. For example, industrial manufacturing plants that produce ammonia for fertilizer produce large amounts of carbon dioxide. Ethanol plants that convert corn or wheat into ethanol produce large amounts of carbon dioxide. Power plants that generate electricity from various resources (e.g., natural gas, coal, other resources) produce large amounts of carbon dioxide. Chemical plants such as nylon production plants, ethylene production plants, and other chemical plants that produce large amounts of carbon dioxide. Some natural gas processing plants produce carbon dioxide as part of the process of purifying the natural gas to meet pipeline specifications. Capturing carbon dioxide for utilization as described herein often involves separating the carbon dioxide from a flue gas stream or another stream where the carbon dioxide is not the major component. Some carbon dioxide sources are already relatively pure and can be used with only minor treatment (which may include gas compression) in the processes described herein. In illustrative embodiment, another source of carbon dioxide can come from cooled combusted stream 174.

System 100 further includes electrolyzer 134 for receiving third heated steam effluent 150 having a temperature of from about 700° C. to about 950° C. or about 750° C. to about 850° C. and second portion 138-2 of cathode effluent 138 having a temperature of from about 700° C. to about 950° C. or about 750° C. to about 850° C. as discussed below into cathode 134-1 and third heated anode purge stream 172 into anode 134-2 where the third heated steam effluent 150 and the second portion 138-2 of cathode effluent 138 participate in a reaction to generate a cathode effluent 138 (composed mainly of $H_2$) from the cathode 134-1 and an anode effluent 136 (oxygen enriched stream) from the anode 134-2. Third heated anode purge stream 172 serves as a purge gas to carry oxygen generated at the anode 134-2. In an illustrative embodiment, electrolyzer 134 can be any suitable high temperature electrolyzer comprising cathode 134-1, anode 134-2 and an electrolyte 134-3 inserted between the cathode 134-1 and the anode 134-2. In a non-limiting illustrative embodiment, electrolyzer 134 is a high temperature solid oxide electrolyzer (also referred to as SOEC) for steam electrolysis comprising:

- a first porous conductive electrode, or "cathode", to be supplied with steam for the production of dihydrogen,
- a second porous conductive electrode, or "anode", via which the dioxygen ($O_2$) produced by the electrolysis of the water injected onto the cathode escapes, and
- a solid oxide membrane (dense electrolyte) sandwiched between the cathode and the anode, the membrane being anionically conductive at high temperatures, usually temperatures above about 700° C. and up to about 950° C.

The electrolyzer 134 may receive input energy (i.e., electricity) from an intermittent source such as solar power (including photovoltaic and reflective), wind power, tidal power, wave power, batteries, and other intermittent energy sources known in the art and combinations thereof. Alternatively, or in addition, electrolyzer 134 may receive input energy from a non-intermittent source, such as an electricity grid (e.g., a regional electricity grid, a municipal electricity grid, or a microgrid), natural gas, coal, nuclear, and other non-intermittent sources known in the art and combinations thereof. The electrolyzer 134 may therefore be electricity connectable to an intermittent energy input, a non-intermittent source, or a combination thereof. In particular embodiments, electrolyzer 134 may receive input energy from the photovoltaic panel.

In some embodiments, electrolyzer 134 may be operational receiving electricity from a photovoltaic panel. At night, electrolyzer 134 may be operated in "hot standby" mode to conserve electricity, or electrolyzer 134 may be electricity connected to another power source to continue operating at night. In particular, electrolyzer 134 may be connected to a power grid such as a regional power grid, a municipal power grid, or a micro grid, and electrolyzer 134 may run when the price of electricity is low.

The system 100 may further comprise an energy storage mechanism or a plurality of energy storage mechanisms. The energy storage mechanism may comprise any mechanism or apparatus operable to store energy such as electricity, thermal energy, etc. For example, the energy storage mechanism may include batteries (e.g., lead-acid batteries, lithium-ion batteries, lithium iron batteries, etc.), ice, water, flywheels, compressed air, pumped hydroelectric, or other energy storage mechanisms known in the art and combinations thereof.

As an overview, for high-temperature steam electrolysis (HTSE), steam ($H_2O$) is injected into the cathode compartment of the electrolyzer. Under the effect of the electrical current applied to the cell, the dissociation of water molecules in the form of steam occurs at the interface between the hydrogen electrode (cathode) and the electrolyte, where this dissociation produces dihydrogen gas ($H_2$) and oxygen ions ($O^{2-}$). Dihydrogen ($H_2$) is collected and discharged at the outlet of the hydrogen compartment. The oxygen ions ($O^{2-}$) migrate through the electrolyte and form dioxygen ($O_2$) at the interface between the electrolyte and the oxygen electrode (anode). A draining gas, such as air, can circulate at the anode and thus collect the oxygen generated in gas form at the anode.

Figure 3:
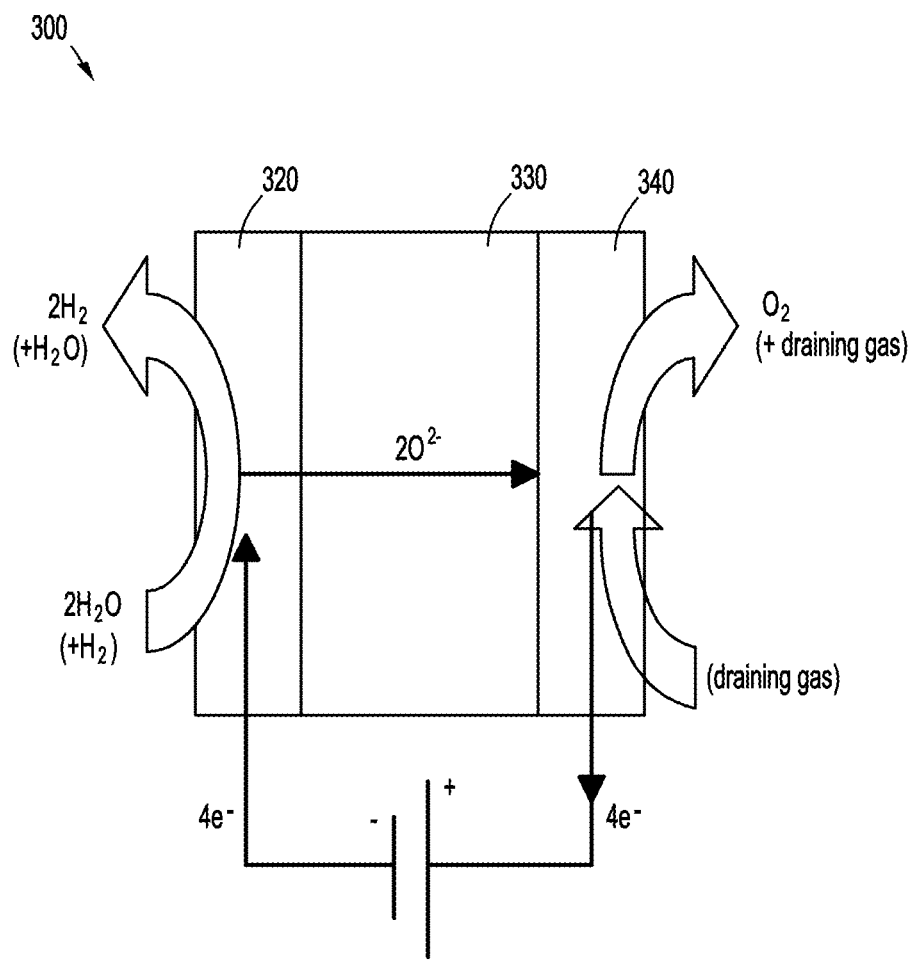
FIG. 3 is a schematic view showing a high-temperature steam electrolysis solid-oxide electrolyzer (SOEC), according to an illustrative embodiment.

In an illustrative embodiment, FIG. 3 shows a schematic view of the principle of operation of a high-temperature solid-oxide electrolyzer (SOEC). Such an electrolyzer is an electrochemical device for producing hydrogen (and oxygen) under the effect of an electrical current. In these electrolyzers, the high-temperature electrolysis of water is performed using steam. Thus, the function of such an electrolyzer is to transform the steam into hydrogen and oxygen according to the following chemical reaction:

$$2H_2O \rightarrow 2H_2 + O_2$$

This reaction occurs electrochemically in the cells of the electrolyzer. As schematically shown in FIG. 3, each basic electrolysis cell 300 is formed by a cathode 320 and an anode 340, placed on either side of a solid electrolyte 330. The two electrodes (i.e., cathode 320 and anode 340) are electronic and/or ionic conductors, made of porous material, and the electrolyte 330 is impervious to gas, an electronic insulator and an ion conductor. The electrolyte 330 may in particular be an anion conductor, and more specifically an anion conductor of $O^{2-}$ ions, and the electrolyzer is then referred to as an anion electrolyzer, by contrast with proton electrolytes ($H^+$).

The electrochemical reactions occur at the interface between each of the electronic conductors and the ion conductor.

At the cathode 320, the half-reaction is as follows:

$$2H_2O + 4e^- \rightarrow 2H_2 + 2O^{2-}.$$

At the anode 340, the half-reaction is as follows:

$$2O^{2-} \rightarrow O_2 + 4e^-.$$

The electrolyte 330, inserted between the two electrodes, i.e., cathode 320 and anode 340, is the site of migration of the $O^{2-}$ ions under the effect of the electrical field created by the difference in potential imposed between anode 340 and cathode 320.

As indicated between parentheses in FIG. 3, the steam at the cathode inlet can be accompanied by hydrogen $H_2$ and the hydrogen produced and recovered at the outlet can be accompanied by steam. Similarly, a draining gas, such as air, may also be injected at the inlet to discharge the oxygen produced. The injection of a draining gas has the additional function of acting as a temperature controller.

A basic electrolyzer, or electrolysis reactor, therefore consists of a basic cell as described above, with a cathode 320, an electrolyte 330, and an anode 340, and two monopolar connectors, which provide electrical, hydraulic and thermal distribution functions.

To increase the flow rates of hydrogen and oxygen produced, a stack of a plurality of basic electrolysis cells one on top of another can be used, separating them with interconnection devices, usually called interconnectors or bipolar interconnection plates. The assembly is positioned between two end interconnection plates that support the electrical and gas supplies of the electrolyzer (electrolysis reactor).

A high-temperature solid-oxide electrolyzer (SOEC) thus comprises at least one, and generally a plurality of electrolysis cells stacked one on top of another, each basic cell being formed by an electrolyte, a cathode and an anode, the electrolyte being inserted between the cathode and the anode.

Thus, the function of a so-called cathode compartment is to distribute the electrical current and steam as well as to recover hydrogen at the cathode in contact.

The function of a so-called anode compartment is to distribute the electrical current and to recover oxygen at the anode in contact, optionally by means of a draining gas.

In some embodiments, the third heated steam effluent 150 and second portion 138-2 of cathode effluent 138 participate in a reaction in a solid oxide electrolytic cell (SOEC) to generate a cathode effluent 138 composed mainly of hydrogen ($H_2$), and an anode effluent 136 composed mainly of oxygen each having a temperature of about 750° C. to about 850° C. For example, the third heated steam effluent 150 and second portion 138-2 of cathode effluent 138 may be reacted at a cathode in the SOEC and the third heated anode purge stream 172 may participate as a purge gas to purge the anode of the SOEC, where the cathode 134-1 and anode 134-2 may be separated by an electrolyte 134-3. In some embodiments, the cathode may operate at a temperature between about 750° C. to about 850° C., and the anode may operate at a temperature between about 750° C. to about 850° C.

In some embodiments, the SOEC may operate at a pressure between about 1 bar to about 20 bars. In some embodiments, the SOEC may operate at a pressure of about 1.02 bar, about 3 bar, about 5 bar, about 7 bar, about 9 bar, about 10 bar, about 15 bar or about 20 bar, where any range from these limits are contemplated herein. In some embodiments, the SOEC may operate at a pressure of about 1 bar to about 3 bar, e.g., about 1 bar, about 1.2 bar, about 1.4 bar, about 1.6 bar, about 1.8 bar, about 2.0 bar, about 2.2 bar, about 2.4 bar, about 2.6 bar, about 2.8 bar or about 3 bar, where any range from these limits are contemplated herein.

The material of the solid oxide electrolyzer electrodes (i.e., cathode and anode) may be based on ceramic materials that exhibit stability through reduction-oxidation (redox) cycles, electrocatalytic activity, and mixed ionic and electronic conductivity in reducing atmospheres. The material of the solid oxide electrodes may be metal or metal oxide-based material (e.g., Ni-based electrodes). In some embodiments, the cathode and anode may be constructed of any suitable material including, for example, $(La,Sr)(Fe,Co)O_3$ (LSCF), $(Sm,Sr)CoO_3$, and Sr-doped $LaMnO_3$ for the anode electrode (anode) and Ni—YSZ, Ni—ScSZ, $La_2NiO_4$, and Ni—$ZrO_2$ for the cathode electrode. Electrode support materials and functional layers include nickel cermets, and other electronic conductors such as $(Sr_{0.8}La_{0.2})TiO_3$(SLT). The electrolyte may be comprised of any suitable material such as, for example, yttria-stabilized zirconia (YSZ), $(La_{0.6}Sr_{0.4})(Ga_{0.8}Mg_{0.2})O_3$(LSGM), Sc-stabilized zirconia (SSZ), and doped ceria. A SOEC cell architecture includes both electrode- and electrolyte-supported cell constructions and ceramic or metallic interconnects. It is to be understood that the above materials are merely exemplary and any known materials for use in the SOEC cell architecture are contemplated.

Referring back to cathode effluent 138, cathode effluent 138 exits the cathode 134-1 of electrolyzer 134 having a temperature of from about 700° C. to about 950° C. or about 750° C. to about 850° C. and acts as a heat transfer medium in heat exchangers 160a and 160b. When exiting the cathode 134-1 of electrolyzer 134, cathode effluent 138 is split into first portion 138-1 and second portion 138-2. Accordingly, first portion 138-1 of cathode effluent 138 delivers the heat in heat exchanger 160a to first heated steam effluent 128 received from heat exchanger 126b to generate a second heated steam effluent 132 having a temperature of from about 550° C. to about 650° C., and the first portion 138-1 of cathode effluent 138 is likewise cooled against first heated steam effluent 128 in heat exchanger 160a to generate a first cooled cathode effluent 156 having a temperature of less than 650° C. such as from about 550° C. to about 630° C.

Second portion 138-2 of cathode effluent 138 can be recycled back to cathode 134-1 where it is combined with incoming third heated steam effluent 150.

System 100 further includes heat exchanger 160b for receiving anode purge stream 110 and first cooled cathode effluent 156 as a heat transfer medium to generate a first heated anode purge stream 140 and a second cooled cathode effluent 158. The received anode purge stream 110 will have a temperature of at or around about 20° C. In other words, first cooled cathode effluent 156 delivers the heat in heat exchanger 160b to anode purge stream 110 and generates first heated anode purge stream 140 having a temperature of from about 350° C. to about 450° C., and the first cooled cathode effluent 156 is likewise cooled against anode purge stream 110 in heat exchanger 160b to generate a second cooled cathode effluent 158 having a temperature of from about 250° C. to about 350° C. In non-limiting illustrative embodiments, anode purge stream 110 is one of air, carbon dioxide or an inert gas such as $N_2$ having a temperature of at or about 20° C. In some embodiments, heat exchanger 160b may be a shell-and-tube, plate-fin, microchannel, spiral wound, or any other suitable heat exchanger.

Second cooled cathode effluent 158 comprises a mixture of hydrogen and water which is separated into a gas portion, referred to as first portion 158-1 which is mainly hydrogen and residual steam, and a liquid water stream upon cooling, referred to as second portion 158-2. First portion 158-1 of second cooled cathode effluent 158 is sent to reactor unit 122 as discussed above. Second portion 158-2 of second cooled cathode effluent 158 is removed from system 100 or recycled back as water feed for SOEC.

In some embodiments, the anode purge stream 110 may be pressurized to produce a pressurized anode purge stream using fans, blowers, compressors or a combination thereof. The air compressor may be centrifugal, mixed-flow, axial-flow, reciprocating, rotary screw, rotary vane, scroll, diaphragm compressor, or a combination thereof. In some embodiments, the pressurized anode purge stream may have a pressure between about 1 bar to about 20 bars. In some embodiments, the pressurized anode purge stream may have a pressure of about 1 bar, about 1.2 bar, about 5 bar, about 10 bar, about 15 bar, or about 20 bar. In some embodiments, the pressurized anode purge stream may have a pressure of from about 1 bar to about 3 bar, e.g., about 1 bar, about 1.2 bar, about 1.4 bar, about 1.6 bar, about 1.8 bar, about 2.0 bar, about 2.2 bar, about 2.4 bar, about 2.6 bar, about 2.8 bar or about 3 bar.

System 100 further includes combustion unit 148 for receiving first reactor tail gas 121-1, second heated steam effluent 132 and oxidizing agent stream 164. First reactor tail gas 121-1 is combusted with oxidizing agent stream 164 to transfer the heat generated in the combustion process to further heat the second heated steam effluent 132 and generate a third heated steam effluent 150 having a temperature of from about 700° C. to about 950° C. or about 750° C. to about 850° C. In illustrative embodiments, the temperature in the combustion unit 148 can range from about 850° C. to about 1200° C. The third heated steam effluent 150 is then sent to the cathode 134-1 of electrolyzer 134 as discussed above. The oxidizing agent stream 164 can be any suitable oxidizing source for combusting first reactor tail gas 121-1. In an illustrative embodiment, the oxidizing source can be air, oxygen, or oxygen diluted with carbon dioxide (i.e., an oxygen enriched source).

In illustrative embodiments, system 100 further includes heat exchanger 170 for receiving second heated anode purge stream 142 and combusted stream 162 as a heat transfer medium to generate a third heated anode purge stream 172 having a temperature of from about 750° C. to about 850° C. and a cooled combusted stream 174. The third heated anode purge stream 172 is then sent to the anode 134-2 of electrolyzer 134 to participate as a purge gas as discussed above in connection with second heated anode purge stream 142. As one skilled in the art will readily appreciate, the composition of cooled combusted stream 174 depends on the particular oxidizing agent used in the combustion process. For example, in one case where the oxidizing source is air, then the combusted stream 174 will contain carbon dioxide, nitrogen and unconverted oxygen. In some embodiments, post treatment can be carried out to separate nitrogen and unconverted oxygen to send the purified carbon dioxide to be combined with carbon dioxide stream 105 or sent downstream for further processing. In another case where the oxidizing source is oxygen or oxygen diluted with carbon dioxide, then cooled combusted stream 174 would contain carbon dioxide and unconverted oxygen, and can be combined with carbon dioxide stream 105 or sent downstream for further processing. In some embodiments, heat exchanger 170 may be a shell-and-tube, plate-fin, microchannel, spiral wound, or any other suitable heat exchanger.

The combustion unit 148 can be any combustion unit wherein a source of carbon can be combusted with oxygen. For example, the combustion unit 148 can be a fired heater or boiler used in power plants or a steam generator or a gas-fired turbine. Those skilled in the art will appreciate that other combustion type reactors may also be utilized and are within the scope of the present disclosure.

In one or more illustrative embodiments, a system processing environment 200 comprises each of the components of system 100 described herein, as well as a controller 210 operatively coupled to system 100. Controller 210 is configured to control operations of one or more of the components of system 100 discussed above. In one illustrative embodiment, controller 210 is configured to actuate one or more of the functionalities of system 100 described herein. For example, controller 210 can comprise one or more processing devices configured to load software instructions from one or more memory devices and execute the software instructions to generate data and/or control signals that can be applied to one or more components of system 100 so as to actuate the functionalities described herein. Actuation of the components by the data and/or control signals may be affected electrically, electromechanically, electrochemically, and/or the like, depending on the nature of the specific component of system 100 being actuated.

Thus, in some embodiments, controller 210 comprises a combination of hardware and software components. For example, the one or more processing devices of controller 210 may comprise one or more microprocessors, one or more microcontrollers, one or more application-specific devices, or other types of processing circuitry, as well as portions or combinations thereof. Further, the one or more memory devices of controller 210 may comprise random access memory (RAM), read-only memory (ROM), or other types of memory, in any combination. It is to be appreciated that the specific architecture of controller 210 is configurable based on the components of system 100 and the functionalities they are intended to perform.

For example, controller 210 can be operatively connected to a processing device in a processing platform which comprises a processor coupled to a memory. The processor may comprise a microprocessor, a microcontroller, an application-specific integrated circuit (ASIC), a field-programmable gate array (FPGA) or other type of processing circuitry, as well as portions or combinations of such circuitry elements. The memory may comprise random access memory (RAM), read-only memory (ROM) or other types of memory, in any combination.

A system and process for the conversion of carbon dioxide to chemicals such as methanol and/or dimethyl ether utilizing a combustion unit, a reverse water gas shift (RWGS) reaction and steam electrolysis with heat integration will now be described with reference to non-limiting embodiment of FIG. 4.

Figure 4:
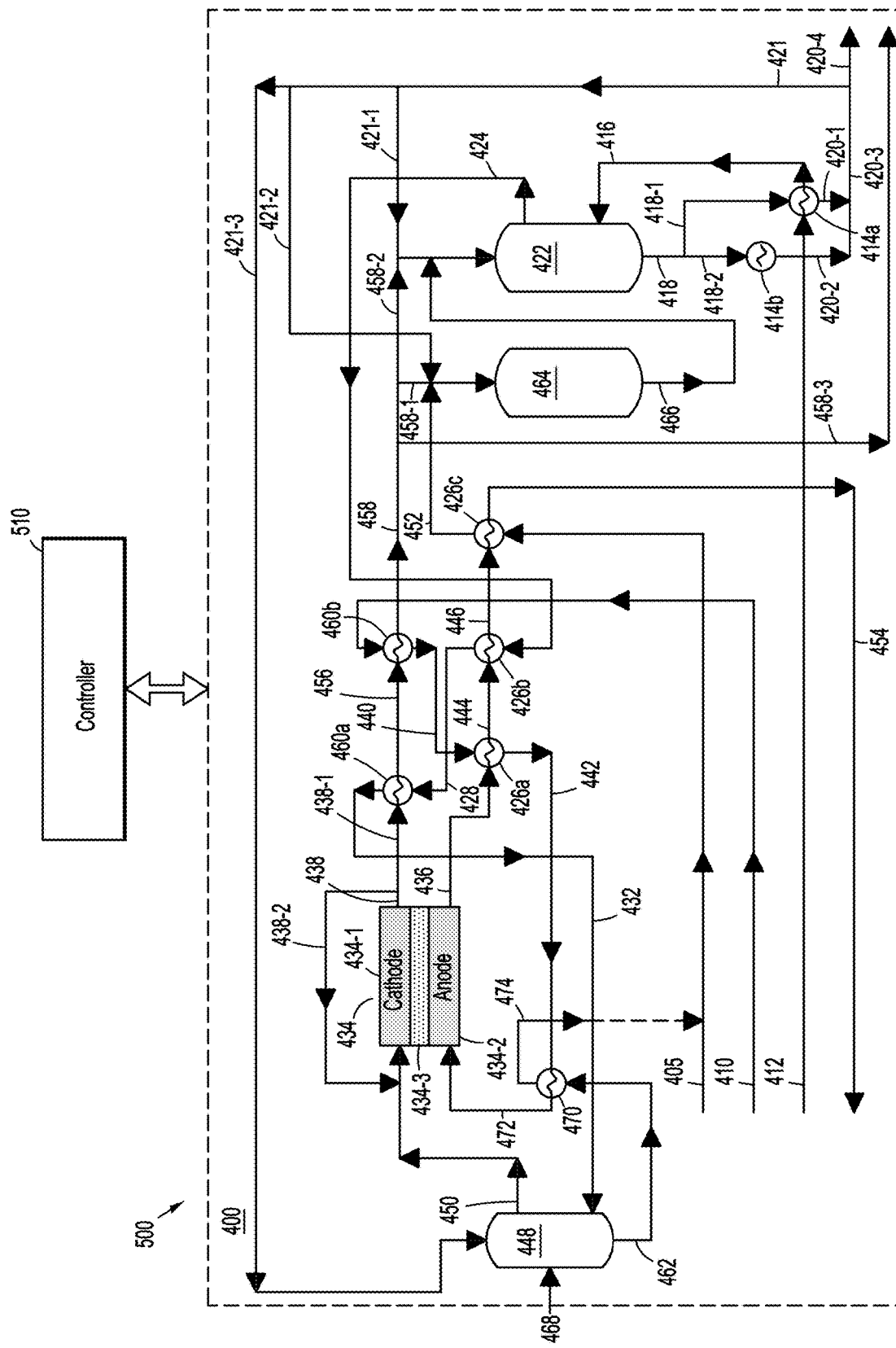
FIG. 4 illustrates a process flow diagram scheme with heat integration design including a combustion unit for a carbon dioxide conversion system for production of methanol/dimethyl ether utilizing a reverse water gas shift (RWGS)

Referring now to FIG. 4, system 400 includes heat exchanger 414a for receiving water feed stream 412 at or around room temperature, i.e., about 20° C., and a first portion 418-1 of reactor synthesis effluent 418 from reactor unit 422 as a heat transfer medium to generate a heated water feed stream effluent 416 having a temperature of about 50° C. to about 150° C. and a cooled reactor synthesis effluent 420-1. In some embodiments, heat exchanger 414a can be any of those discussed above for heat exchanger 114a. The reactor synthesis effluent 418 from reactor unit 422 is a heated reactor synthesis effluent 418 having a temperature of from about 250° C. to about 350° C. which is split into first portion 418-1 and second portion 418-2. Accordingly, first portion 418-1 of reactor synthesis effluent 418 delivers the heat in heat exchanger 414a to water feed stream 412 to generate heated water feed stream effluent 416, and the first portion 418-1 of reactor synthesis effluent 418 is likewise cooled against water feed stream 412 in heat exchanger 414a which cools first portion 418-1 of reactor synthesis effluent 418 to generate a cooled reactor synthesis effluent 420-1, i.e., a temperature of less than 250° C. such as from about 150° C. to about 230° C.

System 400 further includes heat exchanger 414b for receiving second portion 418-2 of reactor synthesis effluent 418 from reactor unit 422 and cooling second portion 418-2 of reactor synthesis effluent 418 to generate a cooled reactor synthesis effluent 420-2 having a temperature of from about 150° C. to about 250° C. In some embodiments, heat exchanger 414b can be any of those discussed above for heat exchanger 114b. In this particular embodiment, cooled reactor synthesis effluent 420-1 and cooled reactor synthesis effluent 420-2 are combined into product stream 420-3 which contains desired products such as methanol, dimethyl ether, undesired by-products such as methane, carbon monoxide and water, and unreacted feeds (i.e., carbon dioxide and hydrogen), syngas etc. The product stream 420-3 containing the desired products and unconverted feeds are separated into product stream 420-4 containing the desired products as a liquid stream, and reactor tail gas 421 as a gaseous stream which primarily contains unconverted hydrogen, and carbon dioxide, and gaseous by-product such as carbon monoxide and methane. The product stream 420-4 can be sent for further downstream processing as known in the art. For example, product stream 420-4 can be sent for further downstream processing for creating high value liquid fuels, such as gasoline, diesel, and jet. In some embodiments, heat exchanger 414b can also be used to heat the first reactor tail gas 421-1 before being recycled to the reactor unit 422.

Reactor tail gas 421 separated from product stream 420-3 has a temperature of from about 30° C. to about 80° C. and is split into a first reactor tail gas 421-1, a second reactor tail gas 421-2 and a third reactor tail gas 421-3. First reactor tail gas 421-1 can be recycled back to reactor unit 422 for further processing with second portion 458-2 of second cooled cathode effluent 458 and reverse water gas shift effluent 466 to enhance overall utilization and conversion of carbon dioxide. Second reactor tail gas 421-2 can be sent to reverse water gas shift (RWGS) reactor unit 464 for further processing with first portion 458-1 of second cooled cathode effluent 458 and heated carbon dioxide effluent 452. Third reactor tail gas 421-3 can be sent to the combustion unit 448 and combusted to provide thermal energy (i.e., heat) to transfer heat to the second heated steam effluent 432 received from heat exchanger 460a to generate a third heated steam effluent 450 for sending to the cathode 434-1 of electrolyzer 434 as a continuous loop in the process and system of the illustrative embodiments as discussed below.

System 400 further includes reactor unit 422 for receiving heated water feed stream effluent 416, first reactor tail gas 421-1, second portion 458-2 of second cooled cathode effluent 458 and a reverse water gas shift effluent 466 including a syngas composed of mostly carbon monoxide (CO) and hydrogen ($H_2$) received from RWGS reactor unit 464 as discussed below. In non-limiting illustrative embodiments, reactor unit 422 can be any of those discussed above for reactor unit 122. The produced methanol/dimethyl ether products can be purified and collected following conventional fractional distillation, while a portion of any unreacted syngas and gaseous byproducts (also referred to as tail gas) can be recycled (see first reactor tail gas 421-1) back to reactor unit 422 as discussed above.

The reverse water gas shift effluent 466 will enter reactor unit 422 having a temperature from about 250° C. to about 350° C. Accordingly, the reaction in reactor unit 422 utilizing at least first reactor tail gas 421-1, second portion 458-2 of second cooled cathode effluent 458 and a reverse water gas shift effluent 466 for making products such as methanol, is an exothermic reaction creating reaction heat to further heat and vaporize the incoming heated water feed stream effluent 416 thereby generating steam feed stream 424 having a temperature of from about 250° C. to about 350° C. The products produced from the reaction process can then be discharged from reactor unit 422 as reactor synthesis effluent 418. Accordingly, for purposes of this illustrative embodiment, reactor synthesis effluent 418 is one or more of methanol and/or dimethyl ether as well as unconverted feeds and by-products such as methane as discussed above. However, this is merely illustrative and any other product that can be made from the conversion of syngas is contemplated herein for use as reactor synthesis effluent 418.

System 400 further includes heat exchangers 426a, 426b and 426c. Heat exchanger 426a receives first heated anode purge stream 440 and anode effluent 436 from the anode 434-2 of electrolyzer 434 as a heat transfer medium to generate a second heated anode purge stream 442 for sending to the anode 434-2 of electrolyzer 434 and a first cooled anode effluent 444 for sending to heat exchanger 426b as discussed below. The anode effluent 436 exits the anode 434-2 of electrolyzer 434 having a temperature of from about 700° C. to about 950° C. or from about 750° C. to about 850° C. Thus, anode effluent 436 delivers the heat in heat exchanger 426a to first heated anode purge stream 440 and generates second heated anode purge stream 442 having a temperature of from about 550° C. to about 650° C., and anode effluent 436 is likewise cooled against first heated anode purge stream 440 in heat exchanger 426a to generate a first cooled anode effluent 444 having a temperature of from about 580° C. to about 680° C. The second heated anode purge stream 442 having a temperature of from about 550° C. to about 650° C., can be further heated to about 750° C. to about 850° C. utilizing combusted stream 462 from the combustion unit 448 as discussed below. In some embodiments, heat exchanger 426a can be any of those discussed above for heat exchanger 126a.

Heat exchanger 426b receives steam feed stream 424 and first cooled anode effluent 444 as a heat transfer medium to generate a first heated steam effluent 428 for sending to heat exchanger 460a and a second cooled anode effluent 446 for sending to heat exchanger 426c as discussed below. In other word, first cooled anode effluent 444 delivers the heat in heat exchanger 426b to steam feed stream 424 and generates first heated steam effluent 428 having a temperature of from about 350° C. to about 450° C., and the first cooled anode effluent 444 is likewise cooled against steam feed stream 424 in heat exchanger 426b to generate a second cooled anode effluent 446 having a temperature of from about 350° C. to about 450° C. In an illustrative embodiment, when anode purge stream 410 is air, then second cooled anode effluent 446 will be composed primarily of oxygen enriched air, e.g., about 50% $O_2$. As another example, when anode purge stream 410 is carbon dioxide, then second cooled anode effluent 446 will be composed of carbon dioxide and oxygen. In some embodiments, heat exchanger 426b can be any of those discussed above for heat exchanger 126b.

Heat exchanger 426c receives carbon dioxide stream 405 having a temperature at or around 20° C. and second cooled anode effluent 446 as a heat transfer medium to generate a heated carbon dioxide effluent 452 for sending to RWGS reactor unit 464 as discussed below and a third cooled anode effluent 454 which exits the system either vented or used as an oxygen enriched stream for combustion processes. In other word, second cooled anode effluent 446 delivers the heat in heat exchanger 426c to carbon dioxide stream 405 and generates heated carbon dioxide effluent 452 having a temperature of from about 250° C. to about 350° C., and the second cooled anode effluent 446 is likewise cooled against carbon dioxide stream 405 in heat exchanger 426c to generate a third cooled anode effluent 454 having a temperature of from about 250° C. to about 350° C. In some embodiments, heat exchanger 426c can be any of those discussed above for heat exchanger 126c. A carbon dioxide source can be any of those discussed above.

System 400 further includes reverse water gas shift (RWGS) reactor unit 464 for receiving heated carbon dioxide effluent 452, first portion 458-1 of second cooled cathode effluent 458 and second reactor tail gas 421-2. The reverse water gas shift reaction is a reaction that allows for conversion of a relatively inert compound ($CO_2$) to a compound that is susceptible to a wider variety of reactions. For example, catalyst and/or reactor configurations for performing Fischer-Tropsch synthesis or methanol synthesis can readily use CO as a reactant but typically cannot use carbon dioxide ($CO_2$). The reverse water gas shift reaction converts $CO_2$ and $H_2$ into CO and $H_2O$. As a result, performing the reverse water gas shift reaction can allow $CO_2$ and $H_2$ to be used to form syngas, which can then be used for a synthesis reaction such as methanol synthesis or dimethyl ether synthesis as discussed above in reactor unit 422.

The reverse water gas shift reaction is part of the same equilibrium as the water gas shift reaction. In that equilibrium, formation of CO and $H_2O$ is favored by increased temperatures. In particular, due to a competing equilibrium reaction for formation of methane, the equilibrium conversion of $CO_2$ passes through a minimum at roughly 600° C. By performing the reverse water gas shift reaction at temperatures of 700° C. or more, or 800° C. or more, or 900° C. or more (such as up to 1600° C. or possibly still higher), the equilibrium conversion of $CO_2$ can be increased while operating at temperatures with relatively fast kinetics. In various aspects, the amount of $CO_2$ in the reaction products can be about 0.5 vol % to about 5.0 vol %, or about 0.5 vol % to about 3.0 vol %, or about 0.5 vol % to about 2.5 vol %, or about 1.0 vol % to about 5.0 vol %, or about 1.0 vol % to about 3.0 vol %, or about 1.0 vol % to about 2.5 vol %.

The RWGS reactor unit 464 can be a cylindrical vessel (e.g., with a length longer than diameter). The entrance to the reactor vessel can be smaller than the overall diameter of the vessel. The reactor vessel can be a steel vessel that is lined with an inert material that is non-reactive with the heated syngas. The steel vessel can be insulated to limit heat loss. Various types of insulation include poured or castable refractory lining or insulating bricks may be used to limit the heat losses to the environment.

A bed of catalyst can be inside the RWGS reactor unit 464. The catalyst can be in the form of granules, pellets, spheres, trilobes, quadra-lobes, monoliths, or any other engineered shape (e.g., to minimize pressure drop across the reactor). The shape and particle size of the catalyst particles can be managed such that pressure drop across the reactor is less than 50 pounds per square inch (psi) (e.g., between 10 psi and 50 psi), and in some cases, less than 20 psi (e.g., between 10 psi and 20 psi). The size of the catalyst form can have a characteristic dimension of between 1 mm to 10 mm. The catalyst particle can be a porous material with an internal surface area greater than about 80 $m^2/g$ (e.g., between about 80 $m^2/g$ and up to about 120 $m^2/g$).

In illustrative embodiments, the RWGS catalyst is a solid solution catalyst that primarily comprises $Ni_2Mg$ impregnated on a high-temperature spinel. This high-performance, solid-solution, Ni-based catalyst can be highly versatile and perform the RWGS reaction efficiently.

In one aspect, the RWGS reactor unit 464 comprises one or more RWGS reactor units, arranged in series e.g., two or more RWGS reactor units. Each of the RWGS reactor units may be either adiabatic or a heated reactor. Heating can be achieved by means of heated carbon dioxide effluent 452, first portion 458-1 of second cooled cathode effluent 458 and second reactor tail gas 421-2 or utilizing heat of combustion.

The reverse water gas shift effluent 466 generated from heated carbon dioxide effluent 452, first portion 458-1 of second cooled cathode effluent 458 and second reactor tail gas 421-2 from the RWGS reactor unit 464 is a stream comprising CO, $H_2O$, unreacted $CO_2$, and $H_2$. The reverse water gas shift effluent 466 can have a temperature from about 400 to about 900° C., depending on the extent of reverse water gas shift reaction and extent of heating. In an illustrative embodiment, the reverse water gas shift effluent 466 can be dehydrated before sending to reactor unit 422.

System 400 further includes electrolyzer 434 for receiving third heated steam effluent 450 having a temperature of from about 700° C. to about 950° C. or from about 750° C. to about 850° C. and second portion 438-2 of cathode effluent 438 having a temperature of from about 700° C. to about 950° C. or from about 750° C. to about 850° C. as discussed below into cathode 434-1 and third heated anode purge stream 472 into anode 434-2 where the third heated steam effluent 450 and second portion 438-2 of cathode effluent 438 participate in a reaction to generate a cathode effluent 438 ($H_2$) from the cathode 434-1 and an anode effluent 436 (oxygen enriched stream) from the anode 434-2. Third heated anode purge stream 472 participates as a purge gas to carry oxygen generated at the anode 434-2. In an illustrative embodiment, electrolyzer 434 can be any suitable high temperature electrolyzer as discussed above for electrolyzer 134 (See, e.g., FIG. 3). As discussed above, the function of such an electrolyzer is to transform the steam into hydrogen and oxygen. In embodiments, electrolyzer 434 can be any suitable high temperature electrolyzer comprising cathode 434-1, anode 434-2 and an electrolyte 434-3 inserted between the cathode 434-1 and the anode 434-2.

Cathode effluent 438 exits the cathode 434-1 of electrolyzer 434 having a temperature of from about 700° C. to about 950° C. or from about 750° C. to about 850° C. and acts as a heat transfer medium in heat exchangers 460a and 460b. When exiting the cathode 434-1 of electrolyzer 434, cathode effluent 438 is split into first portion 438-1 and second portion 438-2. Accordingly, first portion 438-1 of cathode effluent 438 delivers the heat in heat exchanger 460a to first heated steam effluent 428 received from heat exchanger 426b which heats the first heated steam effluent 428 to generate a second heated steam effluent 432 having a temperature of from about 550° C. to about 650° C., and the first portion 438-1 of cathode effluent 438 is likewise cooled against first heated steam effluent 428 in heat exchanger 460a to generate a first cooled cathode effluent 456 having a temperature of less than 650° C. such as from about 550° C. to about 630° C.

Second portion 438-2 of cathode effluent 438 can be recycled back to cathode 434-1 where it is combined with incoming third heated steam effluent 450.

System 400 further includes heat exchanger 460b for receiving anode purge stream 410 and first cooled cathode effluent 456 as a heat transfer medium to generate a first heated anode purge stream 440 and a second cooled cathode effluent 458. The received anode purge stream 410 will have a temperature of at or around about 20° C. In some embodiments, the anode purge stream 410 may be pressurized as discussed above for anode purge stream 110. The first cooled cathode effluent 456 delivers the heat in heat exchanger 460b to anode purge stream 410 and generates first heated anode purge stream 440 having a temperature of from about 350° C. to about 450° C., and the first cooled cathode effluent 456 is likewise cooled against anode purge stream 410 in heat exchanger 460b to generate a second cooled cathode effluent 458 having a temperature of from about 250° C. to about 350° C. In some embodiments, heat exchanger 460b can be any of those discussed above for heat exchanger 160b.

Second cooled cathode effluent 458 comprises a mixture of hydrogen and water which is separated into a gas portion, referred to as first portion 458-1 and second portion 458-2 which are mainly hydrogen and residual steam, and a liquid water stream, referred to as third portion 458-3. First portion 458-1 of second cooled cathode effluent 458 is sent to RWGS reactor unit 464 as discussed above. Second portion 458-2 of second cooled cathode effluent 458 is sent to reactor unit 422 as discussed above. Third portion 458-3 of second cooled cathode effluent 458 is removed from system 400.

System 400 further includes combustion unit 448 for receiving third reactor tail gas 421-3, second heated steam effluent 432 and oxidizing agent stream 468. Third reactor tail gas 421-3 is combusted with oxidizing agent stream 468 to transfer the heat generated in the combustion process to further heat the second heated steam effluent 432 and generate a third heated steam effluent 450 having a temperature of from about 700° C. to about 950° C. or from about 750° C. to about 850° C. The third heated steam effluent 450 is then sent to the cathode 434-1 of electrolyzer 434 as discussed above. The oxidizing agent stream 468 can be any suitable oxidizing source as discussed above for oxidizing agent stream 164. The combustion unit 448 and operating temperatures can be any of those discussed above for combustion unit 148.

In illustrative embodiments, system 400 further includes heat exchanger 470 for receiving second heated anode purge stream 442 and combusted stream 462 as a heat transfer medium to generate a third heated anode purge stream 472 having a temperature of from about 750° C. to about 850° C. and a cooled combusted stream 474. The third heated anode purge stream 472 is then sent to the anode 434-2 of electrolyzer 434 to participate as a purge gas as discussed above. As one skilled in the art will readily appreciate, the composition of cooled combusted stream 474 depends on the particular oxidizing agent used in the combustion process. For example, in one case where the oxidizing source is air, then the cooled combusted stream 474 will contain carbon dioxide, nitrogen and unconverted oxygen. In some embodiments, post treatment can be carried out to separate nitrogen and unconverted oxygen to send the purified carbon dioxide to be combined with carbon dioxide stream 405 or sent downstream for further processing. In another case where the oxidizing source is oxygen or oxygen diluted with carbon dioxide, then cooled combusted stream 474 would contain carbon dioxide and unconverted oxygen, and can be combined with carbon dioxide stream 405 or sent downstream for further processing. In some embodiments, heat exchanger 470 can be any of those discussed above for heat exchanger 170.

In one or more illustrative embodiments, a system processing environment 500 comprises each of the components of system 400 described herein, as well as a controller 510 operatively coupled to system 400. Controller 510 is configured to control operations of one or more of the components of system 400 discussed above. In one illustrative embodiment, controller 510 can be as described as controller 210.

A system and process for the conversion of carbon dioxide to a Fischer-Tropsch product utilizing a reverse water gas shift (RWGS) reaction and hydrogen obtained from steam electrolysis with heat integration will now be described with reference to FIG. 5.

Referring now to FIG. 5, system 600 includes heat exchanger 614a for receiving water feed stream 612 at or around room temperature, i.e., about 20° C., and a first portion 618-1 of Fischer-Tropsch reactor synthesis effluent 618 from Fischer-Tropsch reactor unit 622 as a heat transfer medium to generate a heated water feed stream effluent 616 having a temperature of about 50° C. to about 150° C. and a cooled Fischer-Tropsch reactor synthesis effluent 620-1. In some embodiments, heat exchanger 614a can be any of those discussed above for heat exchanger 114a. The Fischer-Tropsch reactor synthesis effluent 618 from Fischer-Tropsch reactor unit 622 is a heated Fischer-Tropsch reactor synthesis effluent 618 having a temperature of from about 250° C. to about 350° C. which is split into first portion 618-1 and second portion 618-2. Accordingly, first portion 618-1 of Fischer-Tropsch reactor synthesis effluent 618 delivers the heat in heat exchanger 614a to water feed stream 612 to generate heated water feed stream effluent 616, and the first portion 618-1 of Fischer-Tropsch reactor synthesis effluent 618 is likewise cooled against water feed stream 612 in heat exchanger 614a which cools first portion 618-1 of Fischer-Tropsch reactor synthesis effluent 618 to generate a cooled Fischer-Tropsch reactor synthesis effluent 620-1, i.e., a temperature of less than 250° C. such as from about 150° C. to about 230° C.

System 600 further includes heat exchanger 614b for receiving second portion 618-2 of Fischer-Tropsch reactor synthesis effluent 618 from Fischer-Tropsch reactor unit 622 and cooling second portion 618-2 of Fischer-Tropsch reactor synthesis effluent 618 to generate a cooled Fischer-Tropsch reactor synthesis effluent 620-2 having a temperature of from about 150° C. to about 250° C. In some embodiments, heat exchanger 614b can be any of those discussed above for heat exchanger 114b. In this particular embodiment, cooled Fischer-Tropsch reactor synthesis effluent 620-1 and cooled Fischer-Tropsch reactor synthesis effluent 620-2 are combined into Fischer-Tropsch product stream 620-3 which contains Fischer-Tropsch products. For example, the Fischer-Tropsch process involves a series of chemical reactions that produce a variety of hydrocarbons, ideally having the formula ($C_nH_{2n+2}$). In an illustrative embodiment, the more useful reactions produce alkanes such as follows: $(2n+1) H_2 + n\ CO \rightarrow C_nH_{2n+2} + nH_2O$ where n is from 1 to 70. In some embodiments, heat exchanger 614b can also be used to heat the first reactor tail gas 621-1 before being recycled to the Fischer-Tropsch reactor unit 622.

In an illustrative embodiment, the Fischer-Tropsch reactor synthesis effluent 618 resulting in the Fischer-Tropsch product stream 620-3 containing hydrocarbon products such as a $C_1$ to $C_{70}$ hydrocarbon product as the key product together with unreacted syngas and byproducts such as carbon dioxide and produced water. In some embodiments, the system may include a hydrocracker unit and/or fractionation unit (not shown) to upgrade the Fischer-Tropsch liquids. For example, the hydrocracker unit employs a high temperature, high pressure catalytic process that can upgrade heavy Fischer-Tropsch liquid (HFTL) and medium Fischer-Tropsch liquid (MFTL) hydrocarbon streams into a transportation fuel or a blending component meeting chemical and physical properties.

Accordingly, the Fischer-Tropsch product stream 620-3 containing the resulting hydrocarbon products are separated out from gaseous components (also referred to as tail gas) including unreacted syngas and gaseous by-product to form Fischer-Tropsch product stream 620-4 as a liquid stream including at least hydrocarbons and water which is sent for further downstream processing as known in the art. For example, Fischer-Tropsch product stream 620-4 can be sent for further downstream processing for creating high value liquid fuels, such as gasoline, diesel, and jet. The reactor tail gas effluent 621 containing unreacted syngas and gaseous byproducts separated from Fischer-Tropsch product stream 620-3 is split into three streams. First reactor tail gas 621-1 is recycled back to the Fischer-Tropsch reactor unit 622 with second portion 658-2 of second cooled cathode effluent 658 and reverse water gas shift effluent 666 for further processing to increase the overall carbon efficiency. A portion of tail gas effluent 621 can be further processed to obtain a carbon dioxide enriched stream, referred to as carbon dioxide enriched tail gas stream 621-2 composed primarily of carbon dioxide and methane which is sent to reverse water gas shift (RWGS) reactor unit 664 with first portion 658-1 of second cooled cathode effluent 658 and heated carbon dioxide effluent 652 for further carbon monoxide formation. Another portion of tail gas effluent 621 can be further processed to obtain second reactor tail gas 621-3 composed primarily of methane and syngas which is sent to the combustion unit 648 and combusted with an oxidizing agent stream 668 to provide thermal energy to transfer heat to the second heated steam effluent 632 received from heat exchanger 660a to generate a third heated steam effluent 650 for sending to the cathode 634-1 of electrolyzer 634 as a continuous loop in the process and system of the illustrative embodiments as discussed below.

System 600 further includes Fischer-Tropsch reactor unit 622 for heating water feed stream effluent 616, via a Fischer-Tropsch reaction of first reactor tail gas 621-1, second portion 658-2 of second cooled cathode effluent 658 and reverse water gas shift effluent 666 including a syngas composed of mostly carbon monoxide (CO) and hydrogen ($H_2$) received from RWGS reactor unit 664 as discussed below. In non-limiting illustrative embodiments, Fischer-Tropsch reactor unit 622 is a Fischer-Tropsch reactor for converting syngas to a Fischer-Tropsch product by conventional techniques. For example, in a Fischer-Tropsch reaction, syngas composed of carbon monoxide (CO) and hydrogen gas ($H_2$), is converted in the presence of a Fischer-Tropsch catalyst (e.g., iron- or cobalt-based catalyst) into hydrocarbon products, water and other byproducts.

Numerous types of reactor systems have been developed for carrying out the Fischer-Tropsch reaction. For example, Fischer-Tropsch reactor systems include fixed bed reactors, especially multi-tubular fixed bed reactors, fluidized bed reactors, such as entrained fluidized bed reactors, and slurry bed reactors such as three-phase slurry bubble columns and ebullated bed reactors. The present invention is applicable to all types of reactor systems. The reactors each have an inlet for receiving synthesis gas and an outlet for discharging an effluent stream.

The reverse water gas shift effluent 666 will enter Fischer-Tropsch reactor unit 622 having a temperature from about 250° C. to about 350° C. Accordingly, the reaction in Fischer-Tropsch reactor unit 622 utilizing at least first reactor tail gas 621-1, second portion 658-2 of second cooled cathode effluent 658 and reverse water gas shift effluent 666 for making Fischer-Tropsch products is an exothermic reaction creating reaction heat to further heat and vaporize the incoming heated water feed stream effluent 616 thereby generating steam feed stream 624 having a temperature of from about 250° C. to about 350° C. The Fischer-Tropsch products produced from the reaction process can then be discharged from Fischer-Tropsch reactor unit 622 as Fischer-Tropsch reactor synthesis effluent 618.

System 600 further includes heat exchangers 626a, 626b and 626c. Heat exchanger 626a receives first heated anode purge stream 640 and anode effluent 636 from the anode 634-2 of electrolyzer 634 as a heat transfer medium to generate a second heated anode purge stream 642 for sending to the anode 634-2 of electrolyzer 634 and a first cooled anode effluent 644 for sending to heat exchanger 626b as discussed below. The anode effluent 636 exits the anode 634-2 of electrolyzer 634 having a temperature of from about 700° C. to about 950° C. or from about 750° C. to about 850° C. Thus, anode effluent 636 delivers the heat in heat exchanger 626a to first heated anode purge stream 640 and generates second heated anode purge stream 642 having a temperature of from about 550° C. to about 650° C., and anode effluent 636 is likewise cooled against first heated anode purge stream 640 in heat exchanger 626a to generate a first cooled anode effluent 644 having a temperature of from about 580° C. to about 680° C. The second heated anode purge stream 642 having a temperature of from about 550° C. to about 650° C., can be further heated to about 750° C. to about 850° C. utilizing combusted stream 662 from the combustion unit 648 as discussed below. In some embodiments, heat exchanger 626a can be any of those discussed above for heat exchanger 126a.

Heat exchanger 626b receives steam feed stream 624 and first cooled anode effluent 644 as a heat transfer medium to generate a first heated steam effluent 628 for sending to heat exchanger 660a and a second cooled anode effluent 646 for sending to heat exchanger 626c as discussed below. In other word, first cooled anode effluent 644 delivers the heat in heat exchanger 626b to steam feed stream 624 and generates first heated steam effluent 628 having a temperature of from about 350° C. to about 450° C., and the first cooled anode effluent 644 is likewise cooled against steam feed stream 624 in heat exchanger 626b to generate a second cooled anode effluent 646 having a temperature of from about 350° C. to about 450° C. In an illustrative embodiment, when anode purge stream 610 is air, then second cooled anode effluent 646 will be composed primarily of oxygen enriched air, e.g., about 50% $O_2$. As another example, when anode purge stream 610 is carbon dioxide, then second cooled anode effluent 646 will be composed of carbon dioxide and oxygen. In some embodiments, heat exchanger 626b can be any of those discussed above for heat exchanger 126b.

Heat exchanger 626c receives carbon dioxide stream 605 having a temperature at or around 20° C. and second cooled anode effluent 646 as a heat transfer medium to generate a heated carbon dioxide effluent 652 for sending to RWGS reactor unit 664 as discussed below and a third cooled anode effluent 654 which exits the system either vented or used as an oxygen enriched stream for combustion processes. In other word, second cooled anode effluent 646 delivers the heat in heat exchanger 626c to carbon dioxide stream 605 and generates heated carbon dioxide effluent 652 having a temperature of from about 250° C. to about 350° C., and the second cooled anode effluent 646 is likewise cooled against carbon dioxide stream 605 in heat exchanger 626c to generate a third cooled anode effluent 654 having a temperature of from about 250° C. to about 350° C. In some embodiments, heat exchanger 626c can be any of those discussed above for heat exchanger 126c. A carbon dioxide source can be any of those discussed above.

System 600 further includes RWGS reactor unit 664 for receiving heated carbon dioxide effluent 652, first portion 658-1 of second cooled cathode effluent 658 and carbon dioxide enriched tail gas stream 621-2. As discussed above, the reverse water gas shift reaction is a reaction that allows for conversion of a relatively inert compound ($CO_2$) to a compound that is susceptible to a wider variety of reactions. For example, catalyst and/or reactor configurations for performing Fischer-Tropsch synthesis or methanol synthesis can readily use CO as a reactant but typically cannot use carbon dioxide ($CO_2$). The reverse water gas shift reaction converts $CO_2$ and $H_2$ into CO and $H_2O$. As a result, performing the reverse water gas shift reaction can allow $CO_2$ and $H_2$ to be used to form syngas, which can then be used for performing Fischer-Tropsch synthesis as discussed above in Fischer-Tropsch reactor unit 622.

The RWGS reactor unit 664 and the reactions therein can be the same as discussed above for RWGS reactor unit 464.

The reverse water gas shift effluent 666 generated from heated carbon dioxide effluent 652, first portion 658-1 of second cooled cathode effluent 658 and carbon dioxide enriched tail gas stream 621-2 from the RWGS reactor unit 664 is a stream comprising CO, $H_2O$, unreacted $CO_2$, and $H_2$. The reverse water gas shift effluent 666 can have a temperature from about 400 to about 900° C., depending on the extent of reverse water gas shift reaction and extent of heating.

System 600 further includes electrolyzer 634 for receiving third heated steam effluent 650 having a temperature of from about 700° C. to about 950° C. or from about 750° C. to about 850° C. and second portion 638-2 of cathode effluent 638 having a temperature of from about 700° C. to about 950° C. or from about 750° C. to about 850° C. as discussed below into cathode 634-1 and third heated anode purge stream 672 into anode 634-2 where the third heated steam effluent 650 and second portion 638-2 of cathode effluent 638 participate in a reaction to generate a cathode ($H_2$) effluent 638 from the cathode 634-1 and an anode effluent (oxygen enriched stream) 636 from the anode 634-2. Third heated anode purge stream 672 participate as a purge gas to carry oxygen generated at the anode. In an illustrative embodiment, electrolyzer 634 can be any suitable high temperature electrolyzer as discussed above for electrolyzer 134 (See, e.g., FIG. 3). As discussed above, the function of such an electrolyzer is to transform the steam into hydrogen and oxygen. In embodiments, electrolyzer 634 can be any suitable high temperature electrolyzer comprising cathode 634-1, anode 634-2 and an electrolyte 634-3 inserted between the cathode 634-1 and the anode 634-2.

Cathode effluent 638 exits the cathode 634-1 of electrolyzer 634 having a temperature of from about 700° C. to about 950° C. or from about 750° C. to about 850° C. and acts as a heat transfer medium in heat exchangers 660a and 660b. When exiting the cathode 634-1 of electrolyzer 634, cathode effluent 638 is split into first portion 638-1 and second portion 638-2. Accordingly, first portion 638-1 of cathode effluent 638 delivers the heat in heat exchanger 660a to first heated steam effluent 628 received from heat exchanger 626b which heats the first heated steam effluent 628 to generate a second heated steam effluent 632 having a temperature of from about 550° C. to about 650° C., and the first portion 638-1 of cathode effluent 638 is likewise cooled against first heated steam effluent 628 in heat exchanger 660a to generate a first cooled cathode effluent 656 having a temperature of less than 650° C. such as from about 550° C. to about 630° C.

Second portion 638-2 of cathode effluent 638 can be recycled back to cathode 634-1 where it is combined with incoming third heated steam effluent 650.

System 600 further includes heat exchanger 660b for receiving anode purge stream 610 and first cooled cathode effluent 656 as a heat transfer medium to generate a first heated anode purge steam 640 and a second cooled cathode effluent 658. The received anode purge stream 610 will have a temperature of at or around about 20° C. In some embodiments, the anode purge stream 610 may be pressurized as discussed above for anode purge stream 110. First cathode effluent 656 delivers the heat in heat exchanger 660b to anode purge stream 610 and generates first heated anode purge stream 640 having a temperature of from about 350°

C. to about 450° C., and the first cooled cathode effluent 656 is likewise cooled against anode purge stream 610 in heat exchanger 660b to generate second cooled cathode effluent 658 having a temperature of from about 250° C. to about 350° C. In some embodiments, heat exchanger 660b can be any of those discussed above for heat exchanger 160b.

Second cooled cathode effluent 658 comprises a mixture of hydrogen and water which is separated into a gas portion, referred to as first portion 658-1 which is mainly hydrogen and residual steam, and a liquid water stream, referred to as second portion 658-2. First portion 658-1 of second cooled cathode effluent 658 is sent to RWGS reactor unit 664 as discussed above. Second portion 658-2 of second cooled cathode effluent 658 is sent to Fischer-Tropsch reactor unit 622 as discussed above. Third portion 658-3 of second cooled cathode effluent 658 is removed from system 600.

System 600 further includes combustion unit 648 for receiving second reactor tail gas 621-3, second heated steam effluent 632 and oxidizing agent stream 668. Second reactor tail gas 621-3 is combusted with oxidizing agent stream 668 to transfer the heat generated in the combustion process to further heat the second heated steam effluent 632 and generate a third heated steam effluent 650 having a temperature of from about 700° C. to about 950° C. or from about 750° C. to about 850° C. The third heated steam effluent 650 is then sent to the cathode 634-1 of electrolyzer 634 as discussed above. The oxidizing agent stream 668 can be any suitable oxidizing source for combusting second reactor tail gas 621-3.

In illustrative embodiments, system 600 further includes heat exchanger 670 for receiving second heated anode purge stream 642 and combusted stream 662 as a heat transfer medium to generate a third heated anode purge stream 672 having a temperature of from about 750° C. to about 850° C. and a cooled combusted stream 674. The third heated anode purge stream 672 is then sent to the anode 634-2 of electrolyzer 634 to participate as a purge gas. As one skilled in the art will readily appreciate, the composition of combusted stream 662 or cooled combusted stream 674 depends on the particular oxidizing agent used in the combustion process. For example, in one case where the oxidizing source is air, then the combusted stream 662 or cooled combusted stream 674 will contain carbon dioxide, nitrogen and unconverted oxygen. In some embodiments, post treatment can be carried out to separate nitrogen and unconverted oxygen to send the purified carbon dioxide to be combined with carbon dioxide stream 605. In another case where the oxidizing source is oxygen or oxygen diluted with carbon dioxide, then cooled combusted stream 674 would contain carbon dioxide and unconverted oxygen, and can likewise be combined with carbon dioxide stream 605 or sent downstream for further processing. In some embodiments, heat exchanger 670 can be any of those discussed above for heat exchanger 170.

In one or more illustrative embodiments, a system processing environment 700 comprises each of the components of system 600 described herein, as well as a controller 710 operatively coupled to system 600. Controller 710 is configured to control operations of one or more of the components of system 600 discussed above. In one illustrative embodiment, controller 710 can be as described as controller 210.

FIG. 6 illustrates a flow chart of method 800 for each of the starting feed streams including water feed 802, anode purge stream 820 and carbon dioxide feed 830 with heat integration design not including a combustion unit for the conversion of carbon dioxide and steam for production of chemical products such as methanol and dimethyl ether, and/or fuels. In a non-limiting illustrative embodiment, the method utilizing the starting feed streams can be carried out in parallel. Method 800 for the conversion of carbon dioxide and steam for the production of chemical products such as methanol and dimethyl ether and/or fuels according to the illustrative embodiments of the present disclosure will now be described with reference to FIGS. 7A-9B in combination with FIG. 6. FIGS. 7A-9B illustrate heat integration design without the use of a combustion unit for a carbon dioxide conversion system. For ease of understanding, specific examples mentioned in the following description are all illustrative and are not used to limit the scope of the present disclosure.

In an illustrative embodiment, one of the starting streams is water feed 802 at or around a temperature of about 20° C.

Step 804 of method 800 includes water feed 802 being heated by reactor synthesis effluent to generate a heated water stream having a temperature of 50° C. to about 150° C.

Step 806 of method 800 includes heated water stream being heated by reactor synthesis reaction heat to generate a steam feed stream having a temperature of from about 250° C. to about 350° C.

Step 808 of method 800 includes steam feed stream first being heated by an electrolyzer anode effluent to generate a first heated steam feed stream, and then heated by an electrolyzer cathode effluent to generate a second heated steam feed stream.

The second heated steam feed stream is then subjected to either one of steps 810 or 812. Step 810 of method 800 includes second heated steam feed stream being received in the electrolyzer and heated by additional electricity supplied to the electrolyzer to generate a third heated steam feed stream.

Alternative step 812 of method 800 includes second heated steam feed stream being heated by a heat source to generate a third heated steam feed stream.

Step 814 of method 800 includes sending the third heated steam feed stream from step 812 to the electrolyzer.

In an illustrative embodiment, one of the starting streams is anode purge stream 820 at or around a temperature of about 20° C. As discussed below, representative examples of anode purge stream 820 include one or more of air, carbon dioxide or an inert gas such as $N_2$.

Step 822 of method 800 includes anode purge stream first being heated by an electrolyzer cathode effluent to generate a first heated anode purge stream, and then heated by an electrolyzer anode effluent to generate a second anode purge stream.

The second heated anode purge stream is then subjected to either one of steps 824 or 826. Step 824 of method 800 includes second heated anode purge stream being received in the electrolyzer and heated by additional electricity supplied to the electrolyzer to generate a third heated anode purge stream.

Alternative step 826 of method 800 includes second heated anode purge stream being heated by a heat source to generate a third heated anode purge stream.

Step 828 of method 800 includes sending the third heated anode purge stream to the electrolyzer.

In an illustrative embodiment, one of the starting streams is carbon dioxide feed 830 at or around a temperature of about 20° C.

Step 832 of method 800 includes carbon dioxide feed 830 being heated by an electrolyzer anode effluent to generate a heated carbon dioxide feed stream.

Step 834 of method 800 includes sending the heated carbon dioxide feed stream to a synthesis reactor or reverse water gas shift reactor.

FIGS. 7A-9B illustrate an alternative non-limiting illustrative embodiment with heat integration design without a combustion unit for a carbon dioxide conversion system. Referring now to FIG. 7A, system 900 includes heat exchanger 914a for receiving water feed stream 912 at or around room temperature, i.e., about 20° C., and a first portion 918-1 of reactor synthesis effluent 918 from reactor unit 922 as a heat transfer medium to generate a heated water feed stream effluent 916 having a temperature of about 50° C. to about 150° C. and a cooled reactor synthesis effluent 920-1. In some embodiments, heat exchanger 914a can be any of those discussed above for heat exchanger 114a. The reactor synthesis effluent 918 from reactor unit 922 is a heated reactor synthesis effluent 918 having a temperature of from about 250° C. to about 350° C. which is split into first portion 918-1 and second portion 918-2. Accordingly, first portion 918-1 of reactor synthesis effluent 918 delivers the heat in heat exchanger 914a to water feed stream 912 to generate a heated water feed stream effluent 916, and the first portion 918-1 of reactor synthesis effluent 918 is likewise cooled against water feed stream 912 in heat exchanger 914a which cools first portion 918-1 of reactor synthesis effluent 918 to generate a cooled reactor synthesis effluent 920-1, i.e., a temperature of less than 250° C. such as from about 150° C. to about 230° C.

System 900 further includes heat exchanger 914b for receiving second portion 918-2 of reactor synthesis effluent 918 from reactor unit 922 and cooling second portion 918-2 of reactor synthesis effluent 918 to generate a cooled reactor synthesis effluent 920-2 having a temperature of from about 150° C. to about 250° C. In some embodiments, heat exchanger 914b can be any of those discussed above for heat exchanger 114b. In this particular embodiment, cooled reactor synthesis effluent 920-1 and cooled reactor synthesis effluent 920-2 are combined into product stream 920-3 which contains desired products such as methanol, dimethyl ether, undesired by-products such as methane, carbon monoxide, water, and unreacted feeds (i.e., carbon dioxide and hydrogen), syngas etc. The product stream 920-3 containing the desired products and unconverted feeds are separated into product stream 920-4 containing the desired products as a liquid stream, and reactor tail gas 921 as a gaseous stream which primarily contains unconverted hydrogen, and carbon dioxide, and gaseous by-product such as carbon monoxide and methane. The product stream 920-4 can be sent for further downstream processing as known in the art. For example, product stream 920-4 can be sent for further downstream processing for creating high value liquid fuels, such as gasoline, diesel, and jet. In some embodiments, heat exchanger 914b can also be used to heat the reactor tail gas 921 before being recycled to the reactor 922.

Reactor tail gas 921 separated from product stream 920-3 has a temperature of from about 30° C. to about 80° C. and is recycled back to reactor unit 922 for further processing to enhance overall utilization and conversion of carbon dioxide.

System 900 further includes reactor unit 922 for receiving heated water feed stream effluent 916, heated carbon dioxide effluent 952, reactor tail gas 921 and first portion 958-1 of second cooled cathode effluent 958. In non-limiting illustrative embodiments, reactor unit 922 can be any of those discussed above for reactor unit 122. The produced methanol/dimethyl ether products can be purified and collected following conventional fractional distillation, while a portion of any unreacted syngas (also referred to as tail gas) can be recycled (see reactor tail gas 921) back to reactor unit 922 as discussed above.

The heated carbon dioxide effluent 952 will enter reactor unit 922 having a temperature from about 250° C. to about 350° C. and first portion 958-1 of second cooled cathode effluent 958 will enter reactor unit 922 having a temperature from about 250° C. to about 350° C. Accordingly, the reaction in reactor unit 922 utilizing at least heated carbon dioxide effluent 952, reactor tail gas 921 and first portion 958-1 of second cooled cathode effluent 958 for making desired products such as, for example, methanol, is an exothermic reaction creating reaction heat to further heat and vaporize the incoming heated water feed stream effluent 916 thereby generating steam feed stream 924 having a temperature of from about 250° C. to about 350° C. The products produced from the reaction process can then be discharged from reactor unit 922 as reactor synthesis effluent 918. Accordingly, for purposes of this illustrative embodiment, reactor synthesis effluent 918 is one or more of methanol and/or dimethyl ether as well as unconverted feeds and by-products such as methane and water as discussed above. However, this is merely illustrative and any other product that can be made from the conversion of carbon dioxide and hydrogen is contemplated herein for use as reactor synthesis effluent 918.

System 900 further includes heat exchangers 926a, 926b and 926c. Heat exchanger 926a receives first heated anode purge stream 940 and anode effluent 936 from the anode 934-2 of electrolyzer 934 as a heat transfer medium to generate a second heated anode purge stream 942 for sending to the anode 934-2 of electrolyzer 934 and a first cooled anode effluent 944 for sending to heat exchanger 926b as discussed below. The anode effluent 936 exits the anode 934-2 of electrolyzer 934 having a temperature of from about 700° C. to about 950° C. or from about 750° C. to about 850° C. Thus, anode effluent 936 delivers the heat in heat exchanger 926a to first heated anode purge stream 940 and generates second heated anode purge stream 942 having a temperature of from about 550° C. to about 650° C., and anode effluent 936 is likewise cooled against first heated anode purge stream 940 in heat exchanger 926a to generate a first cooled anode effluent 944 having a temperature of from about 580° C. to about 680° C. In some embodiments, second heated anode purge stream 942 has a temperature of from about 550° C. to about 650° C. In some embodiments, heat exchanger 926a can be any of those discussed above for heat exchanger 126a.

Heat exchanger 926b receives steam feed stream 924 and first cooled anode effluent 944 as a heat transfer medium to generate a first heated steam effluent 928 for sending to heat exchanger 960a and a second cooled anode effluent 946 for sending to heat exchanger 926c as discussed below. In other word, first cooled anode effluent 944 delivers the heat in heat exchanger 926b to steam feed stream 924 and generates first heated steam effluent 928 having a temperature of from about 350° C. to about 450° C., and the first cooled anode effluent 944 is likewise cooled against steam feed stream 924 in heat exchanger 926b to generate second cooled anode effluent 946 having a temperature of from about 350° C. to about 450° C. In an illustrative embodiment, when anode purge stream 910 is air, then second cooled anode effluent 946 will be composed primarily of oxygen enriched air, e.g., about 50% $O_2$. As another example, when anode purge stream 910 is carbon dioxide, then second cooled anode effluent 946 will be composed of carbon dioxide and oxygen. In some embodiments, heat exchanger 926b can be any of those discussed above for heat exchanger 126b.

Heat exchanger 926c receives carbon dioxide stream 905 having a temperature at or around 20° C. and second cooled anode effluent 946 as a heat transfer medium to generate a heated carbon dioxide effluent 952 for sending to reverse reactor unit 922 as discussed below and a third cooled anode effluent 954 which exits the system either vented or used as an oxygen enriched stream for combustion processes. In other word, second cooled anode effluent 946 delivers the heat in heat exchanger 926c to carbon dioxide stream 905 and generates heated carbon dioxide effluent 952 having a temperature of from about 250° C. to about 350° C., and the second cooled anode effluent 946 is likewise cooled against carbon dioxide stream 905 in heat exchanger 926c to generate a third cooled anode effluent 954 having a temperature of from about 250° C. to about 350° C. In some embodiments, heat exchanger 926c can be any of those discussed above for heat exchanger 126c. A carbon dioxide source can be any of those discussed above.

System 900 further includes electrolyzer 934 for receiving second heated steam effluent 932 having a temperature of from about 550° C. to about 650° C. and second portion 938-2 of cathode effluent 938 having a temperature of from about 700° C. to about 950° C. or from about 750° C. to about 850° C. as discussed below into cathode 934-1 and second heated anode purge stream 942 having a temperature of from about 550° C. to about 650° C. where the second heated steam effluent 932 and second portion 938-2 of cathode effluent 938 participate in a reaction to generate a cathode effluent 938 from the cathode 934-1 and an anode effluent 936 from the anode 934-2. Second heated anode purge stream 942 participates as a purge gas to carry oxygen generated at the anode 934-2. In an illustrative embodiment, electrolyzer 934 can be any suitable high temperature electrolyzer as discussed above for electrolyzer 134 (See, e.g., FIG. 3). As discussed above, the function of such an electrolyzer is to transform the steam into hydrogen and oxygen. In embodiments, electrolyzer 934 can be any suitable high temperature electrolyzer comprising cathode 934-1, anode 934-2 and an electrolyte 934-3 inserted between the cathode 934-1 and the anode 934-2.

In illustrative embodiments, each of second heated steam effluent 932 and second heated anode purge stream 942 can independently be further heated to an operating temperature of electrolyzer 934 by supplying additional electricity to electrolyzer 934 so that each of second heated steam effluent 932 and second heated anode purge stream 942 will have a temperature of from about 700° C. to about 950° C., or from about 750° C. to about 850° C. As one skilled in the art will readily appreciate, the additional electricity will heat second heated steam effluent 932 in electrolyzer 934 to an operating temperature of electrolyzer 934 such that the further heated second heated steam effluent 932 can participate in a reaction with second portion 938-2 of cathode effluent 938 and produce cathode effluent 938 and anode effluent 936. Likewise, the additional electricity will heat second heated anode purge stream 942 in electrolyzer 934 to an operating temperature of electrolyzer 934 such that the further heated second heated anode purge stream 942 can participate as a purge gas. In embodiment, the additional electricity can be received from an intermittent source such as solar power (including photovoltaic and reflective), wind power, tidal power, wave power, batteries, and other intermittent energy sources known in the art and combinations thereof. Alternatively, or in addition, electrolyzer 934 may receive input energy from a non-intermittent source, such as an electricity grid (e.g., a regional electricity grid, a municipal electricity grid, or a microgrid), natural gas, coal, nuclear, and other non-intermittent sources known in the art and combinations thereof. The electrolyzer 934 may therefore be electricity connectable to an intermittent energy input, a non-intermittent source, or a combination thereof. In particular embodiments, electrolyzer 934 may receive input energy from the photovoltaic panel.

In an alternative embodiment as illustrated in FIG. 7B, each of second heated steam effluent 932 and second heated anode purge stream 942 can be further heated to an operating temperature of electrolyzer 934 by sending second heated steam effluent 932 to a heating unit 970 to generate a third heated steam effluent 972 and second heated anode purge stream 942 to a heating unit 980 to generate a third heated anode purge stream 982 each independently having a temperature of from about 700° C. to about 950° C., or from about 750° C. to about 850° C. Heating units 970 and 980 can be any conventional heating unit known in the art.

In some embodiment, heating unit 970 is a steam heater, and may include a heating element, such as a resistive or inductive heating element. The heating unit 970 is configured to heat the second heated steam effluent 932 to a temperature above the operating temperature of the electrolyzer, i.e., a temperature of from about 700° C. to about 950° C., or from about 750° C. to about 850° C. In another alternate embodiment, the heating unit 970 may include a heat exchanger configured to heat the steam using heat extracted from a high-temperature fluid, such as a fluid heated to about 1200° C. or more. This fluid may be provided from a solar concentrator farm or a power plant. In some embodiments, the heating unit 970 may include multiple steam heater zones with independent power levels (divided vertically or circumferentially or both), in order to enhance thermal uniformity.

In some embodiment, heating unit 980 is an air heater, which may include a resistive or inductive heating element configured to heat the air, carbon dioxide or inert gas to a temperature above the operating temperature of the electrolyzer, i.e., a temperature of from about 700° C. to about 950° C., or from about 750° C. to about 850° C. In alternative embodiments, the heating unit 980 may include a heat exchanger configured to heat the air using heat extracted from a high-temperature fluid, such as a fluid heated to about 1200° C., or more. This fluid may be provided from a solar concentrator farm or a power plant, for example. In some embodiments, the heating unit 980 may include multiple air heater zones with independent power levels (divided vertically or circumferentially or both), in order to enhance thermal uniformity.

Cathode effluent 938 exits the cathode 934-1 of electrolyzer 934 having a temperature of from about 700° C. to about 950° C. or from about 750° C. to about 850° C. and acts as a heat transfer medium in heat exchangers 960a and 960b. When exiting the cathode 934-1 of electrolyzer 934, cathode effluent 938 is split into first portion 938-1 and second portion 938-2. Accordingly, first portion 938-1 of cathode effluent 938 delivers the heat in heat exchanger 960a to first heated steam effluent 928 received from heat exchanger 926b which heats the first heated steam effluent 928 to generate a second heated steam effluent 932 having a temperature of from about 550° C. to about 650° C., and the first portion 938-1 of cathode effluent 938 is likewise cooled against first heated steam effluent 928 in heat exchanger 960a to generate a first cooled cathode effluent 956 having a temperature of less than 650° C. such as from about 550° C. to about 630° C.

Second portion 938-2 of cathode effluent 938 can be recycled back to cathode 934-1 where it is combined with incoming second heated steam effluent 932 (FIG. 7A) or third heated steam effluent 972 (see FIG. 7B).

System 900 further includes heat exchanger 960b for receiving anode purge stream 910 and first cooled cathode effluent 956 as a heat transfer medium to generate a first heated anode purge stream 940 and a second cooled cathode effluent 958. The received anode purge stream 910 will have a temperature of at or around about 20° C. In some embodiments, the anode purge stream 910 may be pressurized as discussed above for anode purge stream 110. The first cooled cathode effluent 956 delivers the heat in heat exchanger 960b to anode purge stream 910 and generates first heated anode purge stream 940 having a temperature of from about 350° C. to about 450° C., and the first cooled cathode effluent 956 is likewise cooled against anode purge stream 910 in heat exchanger 960b to generate second cooled cathode effluent 958 having a temperature of from about 250° C. to about 350° C. In some embodiments, heat exchanger 960b can be any of those discussed above for heat exchanger 160b.

Second cooled cathode effluent 958 comprises a mixture of hydrogen and water which is separated into a gas portion, referred to as first portion 958-1 which is mainly hydrogen and residual steam, and a liquid water stream, referred to as second portion 958-2. First portion 958-1 of second cooled cathode effluent 958 is sent to reactor unit 922 as discussed above. Second portion 958-2 of second cooled cathode effluent 958 is removed from system 900.

In one or more illustrative embodiments, as depicted in FIGS. 7A and 7B, a system processing environment 1000 comprises each of the components of system 900 described herein, as well as a controller 1010 operatively coupled to system 900. Controller 1010 is configured to control operations of one or more of the components of system 900 discussed above. In one illustrative embodiment, controller 1010 can be as described as controller 210.

Referring now to FIG. 8A, system 1100 includes heat exchanger 1114a for receiving water feed stream 1112 at or around room temperature, i.e., about 20° C., and a first portion 1118-1 of reactor synthesis effluent 1118 from reactor unit 1122 as a heat transfer medium to generate a heated water feed stream effluent 1116 having a temperature of about 50° C. to about 150° C. and a cooled reactor synthesis effluent 1120-1. In some embodiments, heat exchanger 1114a can be any of those discussed above for heat exchanger 114a. The reactor synthesis effluent 1118 from reactor unit 1122 is a heated reactor synthesis effluent 1118 having a temperature of from about 250° C. to about 350° C. which is split into first portion 1118-1 and second portion 1118-2. Accordingly, first portion 1118-1 of reactor synthesis effluent 1118 delivers the heat in heat exchanger 1114a to water feed stream 1112 to generate heated water feed stream effluent 1116, and the first portion 1118-1 of reactor synthesis effluent 1118 is likewise cooled against water feed stream 1112 in heat exchanger 1114a which cools first portion 1118-1 of reactor synthesis effluent 1118 to generate cooled reactor synthesis effluent 1120-1, i.e., a temperature of less than 250° C. such as from about 150° C. to about 230° C.

System 1100 further includes heat exchanger 1114b for receiving second portion 1118-2 of reactor synthesis effluent 1118 from reactor unit 1122 and cooling second portion 1118-2 of reactor synthesis effluent 1118 to generate a cooled reactor synthesis effluent 1120-2 having a temperature of from about 150° C. to about 250° C. In some embodiments, heat exchanger 1114b can be any of those discussed above for heat exchanger 114b. In this particular embodiment, cooled reactor synthesis effluent 1120-1 and cooled reactor synthesis effluent 1120-2 are combined into product stream 1120-3 which contains desired products such as methanol, dimethyl ether, undesired by-products such as methane, carbon monoxide, water, and unreacted feeds (i.e., carbon dioxide and hydrogen), syngas etc. The product stream 1120-3 containing the desired products and unconverted feeds are separated into product stream 1120-4 containing the desired products as a liquid stream, and reactor tail gas 1121 as a gaseous stream which primarily contains unconverted hydrogen, and carbon dioxide, and gaseous by-product such as carbon monoxide and methane. The product stream 1120-4 can be sent for further downstream processing as known in the art. For example, product stream 1120-4 can be sent for further downstream processing for creating high value liquid fuels, such as gasoline, diesel, and jet. In some embodiments, heat exchanger 1114b can also be used to heat the first tail gas 1121-1 before being recycled to the reactor unit 1122.

Reactor tail gas 1121 separated from product stream 1120-3 has a temperature of from about 30° C. to about 80° C. and is recycled back to reactor unit 1122 for further processing to enhance overall utilization and conversion of carbon dioxide.

System 1100 further includes reactor unit 1122 for receiving heated water feed stream effluent 1116, first reactor tail gas 1121-1, second portion 1158-2 of second cooled cathode effluent 1158 and a reverse water gas shift effluent 1166 including a syngas composed of mostly carbon monoxide (CO) and hydrogen ($H_2$) received from reverse water gas shift (RWGS) reactor unit 1164 as discussed below. In non-limiting illustrative embodiments, reactor unit 1122 can be any of those discussed above for reactor unit 122. The produced methanol/dimethyl ether products can be purified and collected following conventional fractional distillation, while a portion of any unreacted syngas (also referred to as tail gas) can be recycled (see reactor tail gas 1121-1) back to reactor unit 1122 as discussed above.

The reverse water gas shift effluent 1166 will enter reactor unit 1122 having a temperature from about 250° C. to about 350° C. Accordingly, the reaction in reactor unit 1122 utilizing at least first reactor tail gas 1121-1, second portion 1158-2 of second cooled cathode effluent 1158 and a reverse water gas shift effluent 1166 for making products such as methanol, is an exothermic reaction creating reaction heat to further heat and vaporize the incoming heated water feed stream effluent 1116 thereby generating steam feed stream 1124 having a temperature of from about 250° C. to about 350° C. The products produced from the reaction process can then be discharged from reactor unit 1122 as reactor synthesis effluent 1118. Accordingly, for purposes of this illustrative embodiment, reactor synthesis effluent 1118 is one or more of methanol and/or dimethyl ether as well as unconverted feeds and by-products such as methane as discussed above. However, this is merely illustrative and any other product that can be made from the conversion of syngas is contemplated herein for use as reactor synthesis effluent 1118.

System 1100 further includes heat exchangers 1126a, 1126b and 1126c. Heat exchanger 1126a receives first heated anode purge stream 1140 and anode effluent 1136 from the anode 1134-2 of electrolyzer 1134 as a heat transfer medium to generate a second heated anode purge stream 1142 for sending to the anode 1134-2 of electrolyzer 1134 and a first cooled anode effluent 1144 for sending to heat exchanger 1126b as discussed below. The anode effluent 1136 exits the anode 1134-2 of electrolyzer 1134 having a temperature of from about 700° C. to about 950° C. or from about 750° C. to about 850° C. Thus, anode effluent 1136 delivers the heat in heat exchanger 1126a to first heated anode purge stream 1140 and generates second heated anode purge stream 1142 having a temperature of from about 550° C. to about 650° C., and anode effluent 1136 is likewise cooled against first heated anode purge stream 1140 in heat exchanger 1126a to generate first cooled anode effluent 1144 having a temperature of from about 580° C. to about 680° C.

Heat exchanger 1126b receives steam feed stream 1124 and first cooled anode effluent 1144 as a heat transfer medium to generate a first heated steam effluent 1128 for sending to heat exchanger 1160a and a second cooled anode effluent 1146 for sending to heat exchanger 1126c as discussed below. In other word, first cooled anode effluent 1144 delivers the heat in heat exchanger 1126b to steam feed stream 1124 and generates first heated steam effluent 1128 having a temperature of from about 350° C. to about 450° C., and the first cooled anode effluent 1144 is likewise cooled against steam feed stream 1124 in heat exchanger 1126b to generate second cooled anode effluent 1146 having a temperature of from about 350° C. to about 450° C. In an illustrative embodiment, when anode purge stream 1110 is air, then second cooled anode effluent 1146 will be composed primarily of oxygen enriched air, e.g., about 50% $O_2$. As another example, when anode purge stream 1110 is carbon dioxide, then second cooled anode effluent 1146 will be composed of carbon dioxide and oxygen. In some embodiments, heat exchanger 1126b can be any of those discussed above for heat exchanger 126b.

Heat exchanger 1126c receives carbon dioxide stream 1105 having a temperature at or around 20° C. and second cooled anode effluent 1146 as a heat transfer medium to generate a heated carbon dioxide effluent 1152 for sending RWGS reactor unit 1164 as discussed below and a third cooled anode effluent 1154 which exits the system either vented or used as an oxygen enriched stream for combustion processes. In other word, second cooled anode effluent 1146 delivers the heat in heat exchanger 1126c to carbon dioxide stream 1105 and generates heated carbon dioxide effluent 1152 having a temperature of from about 250° C. to about 350° C., and the second cooled anode effluent 1146 is likewise cooled against carbon dioxide stream 1105 in heat exchanger 1126c to generate third cooled anode effluent 1154 having a temperature of from about 250° C. to about 350° C. In some embodiments, heat exchanger 1126c can be any of those discussed above for heat exchanger 126c. A carbon dioxide source can be any of those discussed above.

System 1100 further includes RWGS reactor unit 1164 for receiving heated carbon dioxide effluent 1152, first portion 1158-1 of second cooled cathode effluent 1158 and second reactor tail gas 1121-2. As discussed hereinabove, the reverse water gas shift reaction is a reaction that allows for conversion of a relatively inert compound ($CO_2$) to a compound that is susceptible to a wider variety of reactions. For example, catalyst and/or reactor configurations for performing Fischer-Tropsch synthesis or methanol synthesis can readily use CO as a reactant but typically cannot use carbon dioxide ($CO_2$). The reverse water gas shift reaction converts $CO_2$ and $H_2$ into CO and $H_2O$. As a result, performing the reverse water gas shift reaction can allow $CO_2$ and $H_2$ to be used to form syngas, which can then be used for a synthesis reaction such as methanol synthesis or dimethyl ether synthesis as discussed above in reactor unit 1122.

The RWGS reactor unit 1164 and the reactions therein can be the same as discussed above for RWGS reactor unit 464.

The reverse water gas shift effluent 1166 generated from heated carbon dioxide effluent 1152, first portion 1158-1 of second cooled cathode effluent 1158 and second reactor tail gas 1121-2 from the RWGS reactor unit 1164 is a stream comprising CO, $H_2O$, unreacted $CO_2$, and $H_2$. The reverse water gas shift effluent 1166 can have a temperature from about 400 to about 900° C., depending on the extent of reverse water gas shift reaction and extent of heating. In an illustrative embodiment, the reverse water gas shift effluent 1166 can be dehydrated before sending to reactor unit 1122.

System 1100 further includes electrolyzer 1134 for receiving second heated steam effluent 1132 having a temperature of from about 550° C. to about 650° C. and second portion 1138-2 of cathode effluent 1138 having a temperature of from about 700° C. to about 950° C. or from about 750° C. to about 850° C. as discussed below into cathode 1134-1 and second heated anode purge stream 1142 having a temperature of from about 550° C. to about 650° C. where the second heated steam effluent 1132 and second portion 1138-2 of cathode effluent 1138 participate in a reaction to generate a cathode effluent 1138 from the cathode 1134-1 and an anode effluent 1136 from the anode 1134-2. Second heated anode purge stream 1142 participates as a purge gas to carry oxygen generated at the anode 1134-2. In an illustrative embodiment, electrolyzer 1134 can be any suitable high temperature electrolyzer as discussed above for electrolyzer 134 (See, e.g., FIG. 3). As discussed above, the function of such an electrolyzer is to transform the steam into hydrogen and oxygen. In embodiments, electrolyzer 1134 can be any suitable high temperature electrolyzer comprising cathode 1134-1, anode 1134-2 and an electrolyte 1134-3 inserted between the cathode 1134-1 and the anode 1134-2.

In illustrative embodiments, each of second heated steam effluent 1132 and second heated anode purge stream 1142 can be further heated to an operating temperature of electrolyzer 1134 by supplying additional electricity to electrolyzer 1134 so that each of second heated steam effluent 1132 and second heated anode purge stream 1142 will independently have a temperature of from about 700° C. to about 950° C., or from about 750° C. to about 850° C. As one skilled in the art will readily appreciate, the additional electricity will heat second heated steam effluent 1132 in electrolyzer 1134 to an operating temperature of electrolyzer 1134 such that the further heated second heated steam effluent 1132 can participate in a reaction with second portion 1138-2 of cathode effluent 1138 and produce cathode effluent 1138 and anode effluent 1136. Likewise, the additional electricity will heat second heated anode purge stream 1142 in electrolyzer 1134 to an operating temperature of electrolyzer 1134 such that the further heated second heated anode purge stream 1142 can participate a purge gas. In an embodiment, the additional electricity can be as discussed above for electrolyzer 934.

In an alternative embodiment as illustrated in FIG. 8B, each of second heated steam effluent 1132 and second heated anode purge stream 1142 can independently be further heated to an operating temperature of electrolyzer 1134 by sending second heated steam effluent 1132 to a heating unit 1170 to generate a third heated steam effluent 1172 and second heated anode purge stream 1142 to a heating unit 1180 to generate a third heated anode purge stream 1182 each independently having a temperature of from about 700° C. to about 950° C., or from about 750° C. to about 850° C. Heating units 1070 and 1080 can be any conventional heating unit known in the art. In some embodiment, heating units 1170 and 1180 can be the same as discussed above for heating units 970 and 980, respectively.

Cathode effluent 1138 exits the cathode 1134-1 of electrolyzer 1134 having a temperature of from about 700° C. to about 950° C. or from about 750° C. to about 850° C. and acts as a heat transfer medium in heat exchangers 1160a and 1160b. When exiting the cathode 1134-1 of electrolyzer 1134, cathode effluent 1138 is split into first portion 1138-1 and second portion 1138-2. Accordingly, first portion 1138-1 of cathode effluent 1138 delivers the heat in heat exchanger 1160a to first heated steam effluent 1128 received from heat exchanger 1126b which heats the first heated steam effluent 1128 to generate a second heated steam effluent 1132 having a temperature of from about 550° C. to about 650° C., and the first portion 1138-1 of cathode effluent 1138 is likewise cooled against first heated steam effluent 1128 in heat exchanger 1160a to generate a first cooled cathode effluent 1156 having a temperature of less than 650° C. such as from about 550° C. to about 630° C.

Second portion 1138-2 of cathode effluent 1138 can be recycled back to cathode 1134-1 where it is combined with incoming second heated steam effluent 1132 (FIG. 8A) or third heated steam effluent 1172 (see FIG. 8B).

System 1100 further includes heat exchanger 1160b for receiving anode purge stream 1110 and first cooled cathode effluent 1156 as a heat transfer medium to generate a first heated anode purge stream 1140 and a second cooled cathode effluent 1158. The received anode purge stream 1110 will have a temperature of at or around about 20° C. In some embodiments, the anode purge stream 1110 may be pressurized as discussed above for anode purge stream 110. The first cooled cathode effluent 1156 delivers the heat in heat exchanger 1160b to anode purge stream 1110 and generates first heated anode purge stream 1140 having a temperature of from about 350° C. to about 450° C., and the first cooled cathode effluent 1156 is likewise cooled against anode purge stream 1110 in heat exchanger 1160b to generate second cooled cathode effluent 1158 having a temperature of from about 250° C. to about 350° C. In some embodiments, heat exchanger 1160b can be any of those discussed above for heat exchanger 160b.

Second cooled cathode effluent 1158 comprises a mixture of hydrogen and water which is separated into a gas portion, referred to as first portion 1158-1 and second portion 1158-2, which are mainly hydrogen and residual steam, and a liquid water stream, referred to as third portion 1158-3. First portion 1158-1 of second cooled cathode effluent 1158 is sent to RWGS reactor unit 1164 as discussed above. Second portion 1158-2 of second cooled cathode effluent 1158 is sent to reactor unit 1122 as discussed above. Third portion 1158-3 of second cooled cathode effluent 1158 is removed from system 1100 or recycled back as water feed.

In one or more illustrative embodiments, as depicted in FIGS. 8A and 8B, a system processing environment 1200 comprises each of the components of system 1100 described herein, as well as a controller 1210 operatively coupled to system 1100. Controller 1210 is configured to control operations of one or more of the components of system 1100 discussed above. In one illustrative embodiment, controller 1210 can be as described as controller 210.

A system and process for the conversion of carbon dioxide to a Fischer-Tropsch product utilizing a reverse water gas shift (RWGS) reaction and hydrogen obtained from steam electrolysis with heat integration will now be described with reference to FIGS. 9A and 9B.

Referring now to FIG. 9A, system 1300 includes heat exchanger 1314a for receiving water feed stream 1312 at or around room temperature, i.e., about 20° C., and a first portion 1318-1 of Fischer-Tropsch reactor synthesis effluent 1318 from Fischer-Tropsch reactor unit 1322 as a heat transfer medium to generate a heated water feed stream effluent 1316 having a temperature of about 50° C. to about 150° C. and a cooled Fischer-Tropsch reactor synthesis effluent 1320-1. In some embodiments, heat exchanger 1314a can be any of those discussed above for heat exchanger 114a. The Fischer-Tropsch reactor synthesis effluent 1318 from Fischer-Tropsch reactor unit 1322 is a heated Fischer-Tropsch reactor synthesis effluent 1318 having a temperature of from about 250° C. to about 350° C. which is split into first portion 1318-1 and second portion 1318-2. Accordingly, first portion 1318-1 of Fischer-Tropsch reactor synthesis effluent 1318 delivers the heat in heat exchanger 1314a to water feed stream 1312 to generate heated water feed stream effluent 1316, and the first portion 1318-1 of Fischer-Tropsch reactor synthesis effluent 1318 is likewise cooled against water feed stream 1312 in heat exchanger 1314a which cools first portion 1318-1 of Fischer-Tropsch reactor synthesis effluent 1318 to generate cooled reactor synthesis effluent 1320-1, i.e., a temperature of less than 250° C. such as from about 150° C. to about 230° C.

System 1300 further includes heat exchanger 1314b for receiving second portion 1318-2 of Fischer-Tropsch reactor synthesis effluent 1318 from Fischer-Tropsch reactor unit 1322 and cooling second portion 1318-2 of Fischer-Tropsch reactor synthesis effluent 1318 to generate a cooled Fischer-Tropsch reactor synthesis effluent 1320-2 having a temperature of from about 150° C. to about 250° C. In some embodiments, heat exchanger 1314b can be any of those discussed above for heat exchanger 114b. In this particular embodiment, cooled Fischer-Tropsch reactor synthesis effluent 1320-1 and cooled Fischer-Tropsch reactor synthesis effluent 1320-2 are combined into Fischer-Tropsch product stream 1320-3 which contains Fischer-Tropsch products as discussed above for Fischer-Tropsch product stream 620-3. In some embodiments, heat exchanger 1314b can also be used to heat the reactor tail gas 1321-1 before being recycled to the Fischer-Tropsch reactor unit 1322.

Accordingly, the Fischer-Tropsch product stream 1320-3 containing the resulting hydrocarbon products are separated out from gaseous components (also referred to as tail gas) including unreacted syngas and gaseous by-product to form Fischer-Tropsch product stream 1320-4 as a liquid stream including at least hydrocarbons and water which is sent for further downstream processing as known in the art. For example, Fischer-Tropsch product stream 1320-4 can be sent for further downstream processing for creating high value liquid fuels, such as gasoline, diesel, and jet. The reactor tail gas 1321 containing unreacted syngas and gaseous byproducts separated from Fischer-Tropsch product stream 1320-3 is split into two streams. For example, reactor tail gas 1321-1 is recycled back to the Fischer-Tropsch reactor unit 1322 for further processing to increase the overall carbon efficiency. In addition, reactor tail gas 1321 can be further processed to obtain a carbon dioxide enriched stream, referred to as carbon dioxide enriched tail gas stream 1321-2 composed primarily of carbon dioxide and methane which is sent to reverse water gas shift (RWGS) reactor unit 1364 for further carbon monoxide formation.

System 1300 further includes Fischer-Tropsch reactor unit 1322 for heating water feed stream effluent 1316, via a Fischer-Tropsch reaction of reactor tail gas 1321-1, second portion 1358-2 of second cooled cathode effluent 1358 and reverse water gas shift effluent 1366 including a syngas composed of mostly carbon monoxide (CO) and hydrogen ($H_2$) received from RWGS reactor unit 1364 as discussed below. In non-limiting illustrative embodiments, Fischer-Tropsch reactor unit 1322 can be the same as discussed above for Fischer-Tropsch reactor unit 622.

The reverse water gas shift effluent 1366 will enter Fischer-Tropsch reactor unit 1322 having a temperature from about 250° C. to about 350° C. Accordingly, the reaction in Fischer-Tropsch reactor unit 1322 utilizing at least reactor tail gas 1321-1, second portion 1358-2 of a second cooled cathode effluent 1358 and reverse water gas shift effluent 1366 for making Fischer-Tropsch products is an exothermic reaction creating reaction heat to further heat and vaporize the incoming heated water feed stream effluent 1316 thereby generating steam feed stream 1324 having a temperature of from about 250° C. to about 350° C. The Fischer-Tropsch products produced from the reaction process can then be discharged from Fischer-Tropsch reactor unit 1322 as Fischer-Tropsch reactor synthesis effluent 1318.

System 1300 further includes heat exchangers 1326a, 1326b and 1326c. Heat exchanger 1326a receives first heated anode purge stream 1340 and anode effluent 1336 from the anode 1334-2 of electrolyzer 1334 as a heat transfer medium to generate a second heated anode purge stream 1342 for sending to the anode 1334-2 of electrolyzer 1334 and a first cooled anode effluent 1344 for sending to heat exchanger 1326b as discussed below. The anode effluent 1336 exits the anode 1334-2 of electrolyzer 1334 having a temperature of from about 700° C. to about 950° C. or from about 750° C. to about 850° C. Thus, anode effluent 1336 delivers the heat in heat exchanger 1326a to first heated anode purge stream 1340 and generates second heated anode purge stream 1342 having a temperature of from about 550° C. to about 650° C., and the anode effluent 1336 is likewise cooled against first heated anode purge stream 1340 in heat exchanger 1326a to generate first cooled anode effluent 1344 having a temperature of from about 580° C. to about 680° C. In some embodiments, heat exchanger 1326a can be any of those discussed above for heat exchanger 126a.

Heat exchanger 1326b receives steam feed stream 1324 and first cooled anode effluent 1344 as a heat transfer medium to generate a first heated steam effluent 1328 for sending to heat exchanger 1360a and a second cooled anode effluent 1346 for sending to heat exchanger 1326c as discussed below. In other word, first cooled anode effluent 1344 delivers the heat in heat exchanger 1326b to steam feed stream 1324 and generates first heated steam effluent 1328 having a temperature of from about 350° C. to about 450° C., and the first cooled anode effluent 1344 is likewise cooled against steam feed stream 1324 in heat exchanger 1326b to generate second cooled anode effluent 1346 having a temperature of from about 350° C. to about 450° C. In an illustrative embodiment, when anode purge stream 1310 is air, then second cooled anode effluent 1346 will be composed primarily of oxygen enriched air, e.g., about 50% $O_2$. As another example, when anode purge stream 1310 is carbon dioxide, then second cooled anode effluent 1346 will be composed of carbon dioxide and oxygen. In some embodiments, heat exchanger 1326b can be any of those discussed above for heat exchanger 126b.

Heat exchanger 1326c receives carbon dioxide stream 1305 having a temperature at or around 20° C. and second cooled anode effluent 1346 as a heat transfer medium to generate a heated carbon dioxide effluent 1352 for sending to RWGS reactor unit 1364 as discussed below and a third cooled anode effluent 1354 which exits the system either vented or used as an oxygen enriched stream for combustion processes. In other word, second cooled anode effluent 1346 delivers the heat in heat exchanger 1326c to carbon dioxide stream 1305 and generates heated carbon dioxide effluent 1352 having a temperature of from about 250° C. to about 350° C., and the second cooled anode effluent 1346 is likewise cooled against carbon dioxide stream 1305 in heat exchanger 1326c to generate third cooled anode effluent 1354 having a temperature of from about 250° C. to about 350° C. In some embodiments, heat exchanger 1326c can be any of those discussed above for heat exchanger 126c. A carbon dioxide source can be any of those discussed above.

System 1300 further includes RWGS reactor unit 1364 for receiving heated carbon dioxide effluent 1352, first portion 1358-1 of second cooled cathode effluent 1358 and carbon dioxide enriched tail gas stream 1321-2. As discussed above, the reverse water gas shift reaction is a reaction that allows for conversion of a relatively inert compound ($CO_2$) to a compound that is susceptible to a wider variety of reactions. For example, catalyst and/or reactor configurations for performing Fischer-Tropsch synthesis or methanol synthesis can readily use CO as a reactant but typically cannot use carbon dioxide ($CO_2$). The reverse water gas shift reaction converts $CO_2$ and $H_2$ into CO and $H_2O$. As a result, performing the reverse water gas shift reaction can allow $CO_2$ and $H_2$ to be used to form syngas, which can then be used for performing Fischer-Tropsch synthesis as discussed above in Fischer-Tropsch reactor unit 1322.

The RWGS reactor unit 1364 and the reactions therein can be the same as discussed above for RWGS reactor unit 464.

The reverse water gas shift effluent 1366 generated from heated carbon dioxide effluent 1352, first portion 1358-1 of second cooled cathode effluent 1358 and carbon dioxide enriched tail gas stream 1321-2 from the RWGS reactor unit 1364 is a stream comprising CO, $H_2O$, unreacted $CO_2$, and $H_2$. The reverse water gas shift effluent 1366 can have a temperature from about 400° C. to about 900° C., depending on the extent of reverse water gas shift reaction and extent of heating.

System 1300 further includes electrolyzer 1334 for receiving second heated steam effluent 1332 having a temperature of from about 550° C. to about 650° C. and second portion 1338-2 of cathode effluent 1338 having a temperature of from about 700° C. to about 950° C. or from about 750° C. to about 850° C. as discussed below into cathode 1334-1 and second heated anode purge stream 1342 having a temperature of from about 550° C. to about 650° C. where the second heated steam effluent 1332 and second portion 1338-2 of cathode effluent 1338 participate in a reaction to generate a cathode effluent 1338 from the cathode 1334-1 and an anode effluent 1336 from the anode 1334-2. Second heated anode purge stream 1342 participates as a purge gas to carry oxygen generated at the anode 1334-2. In an illustrative embodiment, electrolyzer 1334 can be any suitable high temperature electrolyzer as discussed above for electrolyzer 134 (See, e.g., FIG. 3). As discussed above, the function of such an electrolyzer is to transform the steam into hydrogen and oxygen. In embodiments, electrolyzer 1334 can be any suitable high temperature electrolyzer comprising cathode 1334-1, anode 1334-2 and an electrolyte 1334-3 inserted between the cathode 1334-1 and the anode 1334-2.

In illustrative embodiments, each of second heated steam effluent 1332 and second heated anode purge stream 1342 can independently be further heated to an operating temperature of electrolyzer 1334 by supplying additional electricity to electrolyzer 1334 so that each of second heated steam effluent 1332 and second heated anode purge stream 1342 will independently have a temperature of from about 700° C. to about 950° C., or from about 750° C. to about 850° C. As one skilled in the art will readily appreciate, the additional electricity will heat second heated steam effluent 1332 in electrolyzer 1334 to an operating temperature of electrolyzer 1334 such that the further heated second heated steam effluent 1332 can participate in a reaction with second portion 1338-2 of cathode effluent 1338 and produce cathode effluent 1338 and anode effluent 1336. Likewise, the additional electricity will heat second heated anode purge stream 1342 in electrolyzer 1334 to an operating temperature of electrolyzer 1334 such that the further heated second heated anode purge stream 1342 can participate a purge gas. In embodiment, the additional electricity can be as discussed above for electrolyzer 934.

In an alternative embodiment as illustrated in FIG. 9B, each of second heated steam effluent 1332 and second heated anode purge stream 1342 can independently be further heated to an operating temperature of electrolyzer 1334 by sending second heated steam effluent 1332 to a heating unit 1370 to generate a third heated steam effluent 1372 and second heated anode purge stream 1342 to a heating unit 1380 to generate a third heated anode purge stream 1382 each independently having a temperature of from about 700° C. to about 950° C., or from about 750° C. to about 850° C. Heating units 1370 and 1380 can be any conventional heating unit known in the art. In some embodiment, heating units 1370 and 1380 can be the same as discussed above for heating units 970 and 980, respectively.

Cathode effluent 1338 exits the cathode 1334-1 of electrolyzer 1334 having a temperature of from about 700° C. to about 950° C. or from about 750° C. to about 850° C. and acts as a heat transfer medium in heat exchangers 1360a and 1360b. When exiting the cathode 1334-1 of electrolyzer 1334, cathode effluent 1338 is split into first portion 1338-1 and second portion 1338-2. Accordingly, first portion 1338-1 of cathode effluent 1338 delivers the heat in heat exchanger 1360a to first heated steam effluent 1328 received from heat exchanger 1326b which heats the first heated steam effluent 1328 to generate a second heated steam effluent 1332 having a temperature of from about 550° C. to about 650° C., and the first portion 1338-1 of cathode effluent 1338 is likewise cooled against first heated steam effluent 1328 in heat exchanger 1360a to generate a first cooled cathode effluent 1356 having a temperature of less than 650° C. such as from about 550° C. to about 630° C.

Second portion 1338-2 of cathode effluent 1338 can be recycled back to cathode 1334-1 where it is combined with incoming second heated steam effluent 1332 (FIG. 9A) or third heated steam effluent 1372 (see FIG. 9B).

System 1300 further includes heat exchanger 1360b for receiving anode purge stream 1310 and first cooled cathode effluent 1356 as a heat transfer medium to generate a first heated anode purge stream 1340 and a second cooled cathode effluent 1358. The received anode purge stream 1310 will have a temperature of at or around about 20° C. In some embodiments, the anode purge stream 1310 may be pressurized as discussed above for anode purge stream 110. First cooled cathode effluent 1356 delivers the heat in heat exchanger 1360b to anode purge stream 1310 and generates first heated anode purge stream 1340 having a temperature of from about 350° C. to about 450° C., and the first cooled cathode effluent 1356 is likewise cooled against anode purge stream 1310 in heat exchanger 1360b to generate second cooled cathode effluent 1358 having a temperature of from about 250° C. to about 350° C. In some embodiments, heat exchanger 1360b can be any of those discussed above for heat exchanger 160b.

Second cooled cathode effluent 1358 comprises a mixture of hydrogen and water which is separated into a gas portion, referred to as first portion 1358-1 and second portion 1358-2, which are mainly hydrogen and residual steam, and a liquid water stream, referred to as third portion 1358-3. First portion 1358-1 of second cooled cathode effluent 1358 is sent to RWGS reactor unit 1364 as discussed above. Second portion 1358-2 of second cooled cathode effluent 1358 is sent to Fischer-Tropsch reactor unit 1322. Third portion 1358-3 of second cooled cathode effluent 1358 is removed from system 1300 or recycled back as water feed.

In one or more illustrative embodiments, as depicted in FIGS. 9A and 9B, a system processing environment 1400 comprises each of the components of system 1300 described herein, as well as a controller 1410 operatively coupled to system 1300. Controller 1410 is configured to control operations of one or more of the components of system 1300 discussed above. In one illustrative embodiment, controller 1410 can be as described as controller 210.

According to an aspect of the present disclosure, a method, comprises:
heating a steam feed stream having a temperature of from about 250° C. to about 350° C. received from a reactor unit in a first heat exchanger using an anode effluent from an anode of an electrolyzer comprising an anode, a cathode, and an electrolyte inserted between the anode and the cathode as a heat transfer medium to generate a first heated steam effluent having a temperature of about 350° C. to about 450° C. and a cooled anode effluent,
heating the first heated steam effluent in a second heat exchanger using a cathode effluent from the cathode of the electrolyzer as a heat transfer medium to generate a second heated steam effluent having a temperature of about 550° C. to about 650° C. and a cooled cathode effluent,
combusting, in a combustion unit, a first tail gas stream to transfer heat to the second heated steam effluent to generate a third heated steam effluent having a temperature of about 700° C. to about 950° C., and passing the third heated steam effluent to the cathode of the electrolyzer.

In one or more additional illustrative embodiments, as may be combined with the preceding paragraphs, the method further comprises:
heating a water feed stream in a third heat exchanger using a reactor synthesis effluent from the reactor unit as a heat transfer medium to generate a heated water effluent having a temperature of about 50° C. to about 150° C.,
introducing the heated water effluent, a heated carbon dioxide stream, the cooled cathode effluent and a tail gas stream to the reactor unit, and
performing an exothermic reaction of the heated carbon dioxide stream, the cooled cathode effluent and the tail gas stream in the reactor unit, thereby transferring heat from the exothermic reaction to the heated water effluent to generate the steam feed stream.

In one or more additional illustrative embodiments, as may be combined with the preceding paragraphs, where performing an exothermic reaction of the heated carbon dioxide stream, the cooled cathode effluent and the tail gas stream in the reactor unit comprises direct hydrogenation of carbon dioxide to one of methanol or dimethyl ether.

In one or more additional illustrative embodiments, as may be combined with the preceding paragraphs, the method further comprises:

heating a water feed stream in a third heat exchanger using a reactor synthesis effluent from the reactor unit as a heat transfer medium to generate a heated water effluent having a temperature of about 50° C. to about 150° C., introducing the heated water effluent, the cooled cathode effluent, syngas including carbon monoxide and hydrogen received from a reverse water gas shift reaction unit and a tail gas stream to the reactor unit, and performing an exothermic reaction of the cooled cathode effluent, the syngas and the tail gas stream in the reactor unit, thereby transferring heat from the exothermic reaction to the heated water effluent to generate the steam feed stream.

In one or more additional illustrative embodiments, as may be combined with the preceding paragraphs, the method further comprises:

heating a carbon dioxide stream in a third heat exchanger using the cooled anode effluent from the first heat exchanger as a heat transfer medium to generate a heated carbon dioxide effluent having a temperature of about 250° C. to about 350° C., heating an anode purge stream in a fourth heat exchanger using the cooled cathode effluent as a heat transfer medium to generate a first heated anode purge stream having a temperature of about 350° C. to about 450° C. and another cooled cathode effluent, generating syngas by a reverse water gas shift reaction of the heated carbon dioxide effluent, the other cooled cathode effluent and a tail gas stream, and introducing the syngas to the reactor unit.

In one or more additional illustrative embodiments, as may be combined with the preceding paragraphs, where the exothermic reaction in the reactor unit comprises converting the syngas to a chemical product or a fuel.

In one or more additional illustrative embodiments, as may be combined with the preceding paragraphs, where the chemical product is one or more of methanol and dimethyl ether and the fuel is one or more of gasoline, diesel, and jet fuel.

In one or more additional illustrative embodiments, as may be combined with the preceding paragraphs, where the exothermic reaction in the reactor unit comprises converting the syngas to a Fischer-Tropsch product.

In one or more additional illustrative embodiments, as may be combined with the preceding paragraphs, where the exothermic reaction in the reactor unit comprises converting the syngas, the other cooled cathode effluent and the tail gas stream to a reactor synthesis effluent including tail gas, and the method further comprises:

splitting the reaction reactor synthesis effluent into a first reactor synthesis effluent and a second reactor synthesis effluent, heating the water feed stream in the third heat exchanger using the first reactor synthesis effluent as a heat transfer medium to generate the heated water effluent and a cooled first reactor synthesis effluent, cooling the second reactor synthesis effluent in a fourth heat exchanger to generate a cooled second reactor synthesis effluent, combining the cooled first reactor synthesis effluent and the cooled second reactor synthesis effluent to form a third cooled reactor synthesis effluent, separating the tail gas from the third cooled reactor synthesis effluent to generate a third tail gas stream, and passing the third tail gas stream to the combustion unit to generate combustion heat and hot flue gas for further potential heat integration.

In one or more additional illustrative embodiments, as may be combined with the preceding paragraphs, the method further comprises:

heating the first heated anode purge stream in a fifth heat exchanger using the anode effluent from the anode of the electrolyzer as a heat transfer medium to generate a second heated anode purge stream having a temperature of from about 550° C. to about 650° C., and heating the second heated anode purge stream in a sixth heat exchanger using a combustion effluent from the combustion unit as a heat transfer medium to generate a third heated anode purge stream having a temperature of about 700° C. to about 950° C. for sending to the anode of the electrolyzer.

In one or more additional illustrative embodiments, as may be combined with the preceding paragraphs, where the electrolyzer is a solid oxide steam electrolyzer.

According to an aspect of the present disclosure, a method comprises:

heating a water feed stream in a first heat exchanger using a reactor synthesis effluent including tail gas from a reactor unit as a heat transfer medium to generate a heated water effluent having a temperature of about 50° C. to about 150° C., performing an exothermic reaction in the reactor unit thereby transferring heat from the exothermic reaction to the heated water effluent to generate a steam feed stream having a temperature of about 250° C. to about 350° C., heating the steam feed stream in a second heat exchanger using an anode effluent from an anode of an electrolyzer comprising an anode, a cathode, and an electrolyte inserted between the anode and the cathode as a heat transfer medium to generate a first heated steam effluent having a temperature of about 350° C. to about 450° C. and a cooled anode effluent, heating the first heated steam effluent in a third heat exchanger using a cathode effluent from the cathode of the electrolyzer as a heat transfer medium to generate a second heated steam effluent having a temperature of about 550° C. to about 650° C. and a cooled cathode effluent, combusting, in a combustion unit, a first tail gas stream to transfer heat to the second heated steam effluent to generate a third heated steam effluent having a temperature of about 700° C. to about 950° C., and passing the third heated steam effluent to the cathode of the electrolyzer.

In one or more additional illustrative embodiments, as may be combined with the preceding paragraphs, the method further comprises:

heating a carbon dioxide stream in a fourth heat exchanger using the cooled anode effluent from the second heat exchanger as a heat transfer medium to generate a heated carbon dioxide effluent having a temperature of about 250° C. to about 350° C., heating an anode purge stream in a fifth heat exchanger using the cooled cathode effluent from the third heat exchanger as a heat transfer medium to generate a first heated anode purge stream having a temperature of about 350° C. to about 450° C. and another cooled cathode effluent, generating syngas by a reverse water gas shift reaction of the heated carbon dioxide effluent, the other cooled cathode effluent and a tail stream, and introducing the syngas to the reactor unit.

In one or more additional illustrative embodiments, as may be combined with the preceding paragraphs, where the exothermic reaction in the reactor unit comprises converting the syngas to a chemical product or a fuel.

In one or more additional illustrative embodiments, as may be combined with the preceding paragraphs, where the chemical product is one or more of methanol and dimethyl ether and the fuel is one or more of gasoline, diesel, and jet fuel.

In one or more additional illustrative embodiments, as may be combined with the preceding paragraphs, where the exothermic reaction in the reactor unit comprises converting the syngas to a Fischer-Tropsch product.

In one or more additional illustrative embodiments, as may be combined with the preceding paragraphs, where performing an exothermic reaction in the reactor unit comprises direct hydrogenation of a heated carbon dioxide stream, the cooled cathode effluent and a tail gas stream in the reactor unit to generate one of methanol or dimethyl ether.

In one or more additional illustrative embodiments, as may be combined with the preceding paragraphs, where the electrolyzer is a solid oxide steam electrolyzer.

In one or more additional illustrative embodiments, as may be combined with the preceding paragraphs, the method further comprises:

heating the first heated anode purge stream in a sixth heat exchanger using the anode effluent from the anode of the electrolyzer as a heat transfer medium to generate a second heated anode purge stream having a temperature of from about 550° C. to about 650° C., and heating the second heated anode purge stream in a seventh heat exchanger using a combustion effluent from the combustion unit as a heat transfer medium to generate a third heated anode purge stream having a temperature of about 700° C. to about 950° C. for sending to the anode of the electrolyzer.

According to an aspect of the present disclosure, a system comprises:

a first heat exchanger configured to heat a steam feed stream having a temperature of from about 250° C. to about 350° C. using an anode effluent from an anode of an electrolyzer comprising an anode, a cathode, and an electrolyte inserted between the anode and the cathode as a heat transfer medium to generate a first heated steam effluent having a temperature of about 350° C. to about 450° C. and a cooled anode effluent, a second heat exchanger configured to heat the first heated steam effluent using a cathode effluent from a cathode of the electrolyzer as a heat transfer medium to generate a second heated steam effluent having a temperature of about 550° C. to about 650° C. and a first cooled cathode effluent, and a combustion unit configured to combust a tail gas stream to transfer heat to the second heated steam effluent to generate a third heated steam effluent having a temperature of about 700° C. to about 950° C. for sending to the cathode of the electrolyzer to generate another cathode effluent and another anode effluent from the third heated steam effluent.

In one or more additional illustrative embodiments, as may be combined with the preceding paragraphs, the system further comprises:

a third heat exchanger configured to heat an anode purge stream using the first cooled cathode effluent as a heat transfer medium to generate a heated anode purge stream and a second cooled cathode effluent, a fourth heat exchanger configured to heat a carbon dioxide stream using the cooled anode effluent as a heat transfer medium to generate a heated carbon dioxide effluent, and a reactor unit configured to react the heated carbon dioxide effluent, the second cooled cathode effluent and a tail gas stream to produce one or more of methanol or dimethyl ether.

In one or more additional illustrative embodiments, as may be combined with the preceding paragraphs, the system further comprises:

a third heat exchanger configured to heat an anode purge stream using the first cooled cathode effluent as a heat transfer medium to generate a heated anode purge stream and a second cooled cathode effluent, a fourth heat exchanger configured to heat a carbon dioxide stream using the cooled anode effluent as a heat transfer medium to generate a heated carbon dioxide effluent, a reverse water gas shift reaction unit to convert the heated carbon dioxide effluent, the second cooled cathode effluent and a tail gas stream to syngas by a reverse water gas shift reaction, and a reactor unit configured to convert the syngas to one or more of a chemical product or a Fischer-Tropsch product.

In one or more additional illustrative embodiments, as may be combined with the preceding paragraphs, where the electrolyzer is a solid oxide steam electrolyzer.

In one or more additional illustrative embodiments, as may be combined with the preceding paragraphs, the system further comprises:

a fifth heat exchanger configured to heat the first anode purge stream using the anode effluent from the anode of the electrolyzer as a heat transfer medium to generate a second heated anode purge stream having a temperature of from about 550° C. to about 650° C.

In one or more additional illustrative embodiments, as may be combined with the preceding paragraphs, the system further comprises:

a sixth heat exchanger configured to heat the second heated anode purge stream in a seventh heat exchanger using a combustion effluent from the combustion unit as a heat transfer medium to generate a third heated anode purge stream having a temperature of about 700° C. to about 950° C. for sending to the anode of the electrolyzer.

Various features disclosed herein are, for brevity, described in the context of a single embodiment, but may also be provided separately or in any suitable sub-combination. All combinations of the embodiments are specifically embraced by the illustrative embodiments disclosed herein just as if each and every combination was individually and explicitly disclosed. In addition, all sub-combinations listed in the embodiments describing such variables are also specifically embraced by the present compositions and are disclosed herein just as if each and every such sub-combination was individually and explicitly disclosed herein.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A method, comprising:
heating a steam feed stream having a temperature of from about 250° C. to about 350° C. received from a reactor unit in a first heat exchanger using an anode effluent from an anode of an electrolyzer comprising an anode, a cathode, and an electrolyte inserted between the anode and the cathode as a heat transfer medium to generate a first heated steam effluent having a temperature of about 350° C. to about 450° C. and a cooled anode effluent;
heating the first heated steam effluent in a second heat exchanger using a cathode effluent from the cathode of the electrolyzer as a heat transfer medium to generate a second heated steam effluent having a temperature of about 550° C. to about 650° C. and a cooled cathode effluent;
combusting, in a combustion unit, a first tail gas stream to transfer heat to the second heated steam effluent to generate a third heated steam effluent having a temperature of about 700° C. to about 950° C.; and
passing the third heated steam effluent to the cathode of the electrolyzer.

2. The method according to claim 1, further comprising:
heating a water feed stream in a third heat exchanger using a reactor synthesis effluent from the reactor unit as a heat transfer medium to generate a heated water effluent having a temperature of about 50° C. to about 150° C.;
introducing the heated water effluent, a heated carbon dioxide stream, the cooled cathode effluent and a tail gas stream to the reactor unit; and
performing an exothermic reaction of the heated carbon dioxide stream, the cooled cathode effluent and the tail gas stream in the reactor unit, thereby transferring heat from the exothermic reaction to the heated water effluent to generate the steam feed stream.

3. The method according to claim 2, wherein performing an exothermic reaction of the heated carbon dioxide stream, the cooled cathode effluent and the tail gas stream in the reactor unit comprises direct hydrogenation of carbon dioxide to one of methanol or dimethyl ether.

4. The method according to claim 1, further comprising:
heating a water feed stream in a third heat exchanger using a reactor synthesis effluent from the reactor unit as a heat transfer medium to generate a heated water effluent having a temperature of about 50° C. to about 150° C.;
introducing the heated water effluent, the cooled cathode effluent, syngas including carbon monoxide and hydrogen received from a reverse water gas shift reaction unit and a tail gas stream to the reactor unit; and
performing an exothermic reaction of the cooled cathode effluent, the syngas and the tail gas stream in the reactor unit, thereby transferring heat from the exothermic reaction to the heated water effluent to generate the steam feed stream.

5. The method according to claim 1, further comprising:
heating a carbon dioxide stream in a third heat exchanger using the cooled anode effluent from the first heat exchanger as a heat transfer medium to generate a heated carbon dioxide effluent having a temperature of about 250° C. to about 350° C.;
heating an anode purge stream in a fourth heat exchanger using the cooled cathode effluent as a heat transfer medium to generate a first heated anode purge stream having a temperature of about 350° C. to about 450° C. and another cooled cathode effluent;
generating syngas by a reverse water gas shift reaction of the heated carbon dioxide effluent, the other cooled cathode effluent and a tail gas stream; and
introducing the syngas to the reactor unit.

6. The method according to claim 4, wherein the exothermic reaction in the reactor unit comprises converting the syngas to a chemical product or a fuel.

7. The method according to claim 6, wherein the chemical product is one or more of methanol and dimethyl ether and the fuel is one or more of gasoline, diesel, and jet fuel.

8. The method according to claim 4, wherein the exothermic reaction in the reactor unit comprises converting the syngas to a Fischer-Tropsch product.

9. The method according to claim 4, wherein the exothermic reaction in the reactor unit comprises converting the syngas, the cooled cathode effluent and the tail gas stream to a reactor synthesis effluent including tail gas, and the method further comprises:
splitting the synthesis effluent into a first reactor synthesis effluent and a second reactor synthesis effluent;
heating the water feed stream in the third heat exchanger using the first reactor synthesis effluent as a heat transfer medium to generate the heated water effluent and a cooled first reactor synthesis effluent;
cooling the second reactor synthesis effluent in a fourth heat exchanger to generate a cooled second reactor synthesis effluent;
combining the cooled first reactor synthesis effluent and the cooled second reactor synthesis effluent to form a third cooled reactor synthesis effluent;
separating the tail gas from the third cooled reactor synthesis effluent to generate a third tail gas stream; and
passing the third tail gas stream to the combustion unit to generate combustion heat and hot flue gas for further potential heat integration.

10. The method according to claim 5, further comprising:
heating the first heated anode purge stream in a fifth heat exchanger using the anode effluent from the anode of the electrolyzer as a heat transfer medium to generate a second heated anode purge stream having a temperature of from about 550° C. to about 650° C.; and
heating the second heated anode purge stream in a sixth heat exchanger using a combustion effluent from the combustion unit as a heat transfer medium to generate a third heated anode purge stream having a temperature of about 700° C. to about 950° C. for sending to the anode of the electrolyzer.

11. The method according to claim 1, wherein the electrolyzer is a solid oxide steam electrolyzer.

12. A method, comprising:
heating a water feed stream in a first heat exchanger using a reactor synthesis effluent including tail gas from a reactor unit as a heat transfer medium to generate a heated water effluent having a temperature of about 50° C. to about 150° C.;
performing an exothermic reaction in the reactor unit thereby transferring heat from the exothermic reaction to the heated water effluent to generate a steam feed stream having a temperature of about 250° C. to about 350° C.;
heating the steam feed stream in a second heat exchanger using an anode effluent from an anode of an electrolyzer comprising an anode, a cathode, and an electrolyte inserted between the anode and the cathode as a heat transfer medium to generate a first heated steam effluent having a temperature of about 350° C. to about 450° C. and a cooled anode effluent;

heating the first heated steam effluent in a third heat exchanger using a cathode effluent from the cathode of the electrolyzer as a heat transfer medium to generate a second heated steam effluent having a temperature of about 550° C. to about 650° C. and a cooled cathode effluent;

combusting, in a combustion unit, a first tail gas stream to transfer heat to the second heated steam effluent to generate a third heated steam effluent having a temperature of about 700° C. to about 950° C.; and passing the third heated steam effluent to the cathode of the electrolyzer.

13. The method according to claim 12, further comprising:

heating a carbon dioxide stream in a fourth heat exchanger using the cooled anode effluent from the second heat exchanger as a heat transfer medium to generate a heated carbon dioxide effluent having a temperature of about 250° C. to about 350° C.;

heating an anode purge stream in a fifth heat exchanger using the cooled cathode effluent from the third heat exchanger as a heat transfer medium to generate a first heated anode purge stream having a temperature of about 350° C. to about 450° C. and another cooled cathode effluent;

generating syngas by a reverse water gas shift reaction of the heated carbon dioxide effluent, the other cooled cathode effluent and a tail stream; and introducing the syngas to the reactor unit.

14. The method according to claim 13, further comprising:

heating the first heated anode purge stream in a sixth heat exchanger using the anode effluent from the anode of the electrolyzer as a heat transfer medium to generate a second heated anode purge stream having a temperature of from about 550° C. to about 650° C.; and heating the second heated anode purge stream in a seventh heat exchanger using a combustion effluent from the combustion unit as a heat transfer medium to generate a third heated anode purge stream having a temperature of about 700° C. to about 950° C. for sending to the anode of the electrolyzer.

15. The method according to claim 13, wherein the exothermic reaction in the reactor unit comprises converting the syngas to a chemical product or a fuel.

16. The method according to claim 13, wherein the exothermic reaction in the reactor unit comprises converting the syngas to a Fischer-Tropsch product.

17. The method according to claim 12, wherein performing an exothermic reaction in the reactor unit comprises direct hydrogenation of a heated carbon dioxide stream, the cooled cathode effluent and a tail gas stream in the reactor unit to generate one of methanol or dimethyl ether.

18. The method according to claim 12, wherein the electrolyzer is a solid oxide steam electrolyzer.

* * * * *